(12) United States Patent
Forrest

(10) Patent No.: US 11,986,519 B2
(45) Date of Patent: May 21, 2024

(54) HAEMOPHILUS INFLUENZAE SACCHARIDE-CARRIER CONJUGATE COMPOSITIONS AND USES THEREOF

(71) Applicant: Eva Barbara Schadeck, South Nyack, NY (US)

(72) Inventor: Bruce D. Forrest, South Nyack, NY (US)

(73) Assignee: Eva Barbara Schadeck, South Nyack, NY (US)

( * ) Notice: Subject to any disclaimer, the term of this patent is extended or adjusted under 35 U.S.C. 154(b) by 0 days.

(21) Appl. No.: 17/569,304

(22) Filed: Jan. 5, 2022

(65) Prior Publication Data

US 2022/0323566 A1    Oct. 13, 2022

Related U.S. Application Data

(63) Continuation of application No. 16/482,632, filed as application No. PCT/US2018/016563 on Feb. 2, 2018, now Pat. No. 11,246,918.

(60) Provisional application No. 62/454,598, filed on Feb. 3, 2017.

(51) Int. Cl.
| | |
|---|---|
| *A61K 39/00* | (2006.01) |
| *A61K 39/102* | (2006.01) |
| *A61P 31/04* | (2006.01) |

(52) U.S. Cl.
CPC ............ *A61K 39/102* (2013.01); *A61P 31/04* (2018.01); *A61K 2039/55505* (2013.01); *A61K 2039/575* (2013.01); *A61K 2039/6018* (2013.01); *A61K 2039/6037* (2013.01); *A61K 2039/6068* (2013.01)

(58) Field of Classification Search
CPC .................................................. A61K 39/102
See application file for complete search history.

(56) References Cited

U.S. PATENT DOCUMENTS

| | | |
|---|---|---|
| 4,220,717 A | 9/1980 | Kuo |
| 4,459,286 A | 7/1984 | Hilleman et al. |
| 4,496,538 A | 1/1985 | Gordon |
| 4,644,059 A | 2/1987 | Gordon |
| 4,673,574 A | 6/1987 | Anderson |
| 4,686,102 A | 8/1987 | Ritchey et al. |
| 4,902,506 A | 2/1990 | Anderson et al. |
| 5,097,020 A | 3/1992 | Anderson et al. |
| 5,192,540 A | 3/1993 | Kuo et al. |
| 5,360,897 A | 11/1994 | Anderson et al. |
| 5,445,817 A | 8/1995 | Schneerson et al. |
| 5,614,382 A | 3/1997 | Metcalf |
| 5,623,057 A | 4/1997 | Marburg et al. |
| 5,695,768 A | 12/1997 | Malcolm |
| 5,965,714 A | 10/1999 | Ryall |
| 6,451,317 B1 | 9/2002 | Blake et al. |
| 7,018,637 B2 | 3/2006 | Chong et al. |
| 7,709,001 B2 | 5/2010 | Hausdorff et al. |
| 7,955,605 B2 | 6/2011 | Prasad |
| 8,192,746 B2 | 6/2012 | Caulfield et al. |
| 8,808,707 B1 | 8/2014 | Siber et al. |
| 8,808,708 B2 | 8/2014 | Hausdorff et al. |
| 8,895,024 B2 | 11/2014 | Hausdorff et al. |
| 9,107,872 B2 | 8/2015 | Biemans et al. |
| 9,248,197 B2 | 2/2016 | Lees |
| 9,492,559 B2 | 11/2016 | Emini et al. |
| 9,782,467 B2 | 10/2017 | Constantino |
| 10,124,050 B2 | 11/2018 | Watson et al. |
| 10,716,848 B2 | 7/2020 | Hausdorff et al. |
| 11,246,918 B2 | 2/2022 | Forrest |
| 2005/0214329 A1 | 9/2005 | Laferriere et al. |
| 2008/0206276 A1 | 8/2008 | Otto et al. |
| 2009/0010959 A1 | 1/2009 | Biemans et al. |
| 2009/0017059 A1 | 1/2009 | Beimans et al. |
| 2016/0324949 A1 | 11/2016 | Han et al. |
| 2019/0343948 A1 | 11/2019 | Forrest |

FOREIGN PATENT DOCUMENTS

| | | |
|---|---|---|
| EP | 0338265 B1 | 5/1994 |
| WO | WO 2003/051392 A2 | 6/2003 |
| WO | WO 2007/051004 A2 | 5/2007 |
| WO | WO 2013/178236 A1 | 12/2013 |
| WO | WO 2016/113644 A1 | 7/2016 |

OTHER PUBLICATIONS

International Search Report and Written Opinion mailed on Jun. 26, 2019, in connection with Application No. PCT/US2018/016563.
International Preliminary Report on Patentability mailed on Aug. 15, 2019, in connection with Application No. PCT/US2018/016563.
[No Author Listed], Decision Denying Institution of *Inter Partes* Review 37 C.F.R. § 42.108. Case IPR2017-01223. U.S. Pat. No. 9,399,060 B2. Paper 8. Oct. 20, 2017. 22 pages.
Albani et al., Polysaccharide purification from *Haemophilus influenzae* type b through tangential microfiltration. Carbohydr Polym. Feb. 13, 2015;116:67-73. doi: 10.1016/j.carbpol.2014.03.046. Epub Mar. 28, 2014.

(Continued)

*Primary Examiner* — Albert M Navarro
(74) *Attorney, Agent, or Firm* — Wolf, Greenfield & Sacks, P.C.

(57) ABSTRACT

Provided herein are *Haemophilus influenzae* saccharide-carrier conjugates and compositions thereof. Also provided are methods of making and using the conjugates and compositions thereof, and kits containing the conjugates. *Haemophilus influenzae* saccharide-lipid conjugates, *Haemophilus influenzae* saccharide-glycosphingolipid conjugates, compositions containing these, methods of making and using the conjugates and compositions, and kits containing these, are also disclosed. Saccharide-lipid conjugates, and saccharide-glycosphingolipid conjugates comprising saccharides from *Haemophilus influenzae* serotype a, as well as compositions containing these, methods of making and using the conjugates and compositions, and kits containing these, are also disclosed.

20 Claims, No Drawings

(56) References Cited

OTHER PUBLICATIONS

Branefors-Helander P., The structure of the capsular antigen from *Haemophilus influenzae* type A. Carbohydr Res. Jun. 1977;56(1):117-22.

Branefors-Helander et al., Structural studies of the capsular antigen of *Haemophilus influenzae* type c. Carbohydr Res. Nov. 1979;76:197-202. doi: 10.1016/0008-6215(79)80018-x.

Branesfors-Helander et al., Structural studies of the capsular antigen from *Haemophilus influenzae* type f. Carbohydr Res. Mar. 1980;79(2):308-12. doi: 10.1016/s0008-6215(00)83845-8.

Branesfors-Helander et al., Structural studies of the capsular polysaccharide elaborated by *Haemophilus influenza* type d. Carbohydr Res. Nov. 16, 1981;97(2):285-91. doi: 10.1016/s0008-6215(00)80674-6.

Branesfors-Helander P., Structural studies of two capsular polysaccharides elaborated by different strains of *Haemophilus influenzae* type e. Carbohydr Res. Jan. 15, 1981;88(1):77-84. doi: 10.1016/s0008-6215(00)84602-9.

Byrd et al., New n.m.r.-spectroscopic approaches for structural studies of polysaccharides: application to the *Haemophilus influenzae* type a capsular polysaccharide. Carbohydr Res. Aug. 15, 1987;166(1):47-58. doi: 10.1016/0008-6215(87)80043-5.

Campos et al., Infections due to *Haemophilus influenzae* serotype E: microbiological, clinical, and epidemiological features. Clin Infect Dis. Sep. 15, 2003;37(6):841-5. doi: 10.1086/377232. Epub Aug. 28, 2003.

Cox et al., Investigating the candidacy of a capsular polysaccharide-based glycoconjugate as a vaccine to combat *Haemophilus influenzae* type a disease: A solution for an unmet public health need. Vaccine. Oct. 27, 2017;35(45):6129-6136. doi: 10.1016/j.vaccine.2017.09.055. Epub Sep. 23, 2017.

Egan et al., Structural and immunological studies of the *Haemophilus influenzae* type c capsular polysaccharide. Carbohydr. Res. Apr. 15, 1980; 80(2):305-16.

Forsee et al., Characterization of the lipid linkage region and chain length of the cellubiuronic acid capsule of *Streptococcus pneumoniae*. J Biol Chem. May 1, 2009;284(18):11826-35. doi: 10.1074/jbc.M900386200. Epub Feb. 19, 2009.

Frasch, Analytical and Manufacturing Challenges: Preparation of Bacterial Polysaccharide Conjugates. Vaccine Technology III. Session IV: Conjugate Vaccines. Albufeira, Portugal. Jun. 1-6, 2008. 20 pages.

Hsieh CL, Characterization of saccharide-CRM197 conjugate vaccines. Dev Biol (Basel). 2000;103:93-104.

Jin et al., *Haemophilus influenzae* type a infection and its prevention. Infect Immun. Jun. 2007;75(6):2650-4. doi: 10.1128/IAI.01774-06. Epub Mar. 12, 2007.

Kayhty et al., The protective level of serum antibodies to the capsular polysaccharide of *Haemophilus influenzae* type b. J Infect Dis. Jun. 1983;147(6):1100. doi: 10.1093/infdis/147.6.1100.

Konini et al., Dynamics of naturally acquired antibody against *Haemophilus influenzae* type a capsular polysaccharide in a Canadian Aboriginal population. Prev Med Rep. Jan. 26, 2016;3:145-50. doi: 10.1016/j.pmedr.2016.01.004.

Konini et al., Modelling the impact of vaccination on curtailing *Haemophilus influenzae* serotype 'a'. J Theor Biol. Dec. 21, 2015;387:101-10. doi: 10.1016/j.jtbi.2015.09.026. Epub Oct. 8, 2015.

Ladhani et al., Invasive *Haemophilus influenzae* serotype e and f disease, England and Wales. Emerg Infect Dis. May 2012;18(5):725-32. doi: 10.3201/eid1805.111738.

Lam et al., Sequence analysis of serotype-specific synthesis regions II of *Haemophilus influenzae* serotypes c and d: evidence for common ancestry of capsule synthesis in *Pasteurellaceae* and *Neisseria meningitidis*. Res Microbiol. Jun. 2011;162(5):483-7. doi: 10.1016/j.resmic.2011.04.002. Epub Apr. 7, 2011.

Pozsgay et al., Protein conjugates of synthetic saccharides elicit higher levels of serum IgG lipopolysaccharide antibodies in mice than do those of the O-specific polysaccharide from *Shigella dysenteriae* type 1. Proc Natl Acad Sci U S A. Apr. 27, 1999;96(9):5194-7. doi: 10.1073/pnas.96.9.5194.

St. Michael et al., Investigating the candidacy of LPS-based glycoconjugates to prevent invasive meningococcal disease: conjugates based on core oligosaccharides. Glycoconj J. Jan. 2014;31(1):25-39. doi: 10.1007/s10719-013-9500-z. Epub Sep. 7, 2013.

Sutton et al., Differential complement resistance mediates virulence of *Haemophilus influenzae* type b. Infect Immun. Jan. 1982;35(1):95-104. doi: 10.1128/IAI.35.1.95-104.1982.

Swift et al., Complement-mediated serum activities against genetically defined capsular transformants of *Haemophilus influenzae*. Microb Pathog. Apr. 1991;10(4):261-9. doi: 10.1016/0882-4010(91)90010-8.

Szu et al., Ultrasonic irradiation of bacterial polysaccharides. Characterization of the depolymerized products and some applications of the process. Carbohydr Res. Sep. 1, 1986;152:7-20. doi: 10.1016/s0008-6215(00)90283-0.

Tsui et al., Structural studies of the *Haemophilus influenzae* type e capsular polysaccharide. Carbohydr Res. Jan. 15, 1981;88(1):85-92. doi: 10.1016/s0008-6215(00)84603-0.

Van Den Biggelaar et al., Immunization of newborns with bacterial conjugate vaccines. Vaccine. May 17, 2013;31(21):2525-30. doi: 10.1016/j.vaccine.2012.06.019. Epub Jun. 19, 2012.

Yildirim et al., Structural analysis of lipopolysaccharides from *Haemophilus influenzae* serotype f. Structural diversity observed in three strains. Eur J Biochem. Aug. 2003;270(15):3153-67. doi: 10.1046/j.1432-1033.2003.03693.x.

HAEMOPHILUS INFLUENZAE SACCHARIDE-CARRIER CONJUGATE COMPOSITIONS AND USES THEREOF

RELATED APPLICATIONS

This application is a continuation of and claims priority under 35 U.S.C. § 120 to U.S. patent application U.S. Ser. No. 16/482,632, filed Jul. 31, 2019, which is a national stage filing under 35 U.S.C. § 371 of International PCT Application, PCT/US2018/016563, filed Feb. 2, 2018, which claims priority under 35 U.S.C. § 119(e) to U.S. provisional application, U.S. Ser. No. 62/454,598, filed Feb. 3, 2017, each of which is incorporated by reference herein in their entirety.

FIELD OF THE INVENTION

The disclosure provides *Haemophilus influenzae* saccharide-carrier conjugates and pharmaceutical compositions comprising *Haemophilus influenzae* saccharide-carrier conjugates, including *Haemophilus influenzae* saccharide-polypeptide conjugates, *Haemophilus influenzae* saccharide-glycosphingolipid conjugates, and *Haemophilus influenzae* saccharide-lipid conjugates. Also provided are methods of making and using *Haemophilus influenzae* saccharide-carrier conjugates and compositions thereof. Further provided herein are kits comprising *Haemophilus influenzae* saccharide-carrier conjugates and compositions thereof.

BACKGROUND

*Haemophilus influenzae* is a Gram-negative bacterium that causes a wide range of localized and invasive infection. The structure of capsular polysaccharides surrounding *H. influenzae* are used to categorize *H. influenzae* strains into six distinct serotypes a-f, although *H. influenzae* strains exist that do not belong to the identified serotypes. Individuals may be at risk of *H. influenzae* infection due to the geographic prevalence of specific serotypes as well as the lack of cross-protection between *H. influenzae* serotypes.

SUMMARY

The present disclosure provides immunogenic saccharide-carrier conjugates comprising saccharides from *Haemophilus influenzae*, including *Haemophilus influenzae* serotype a. Also provided herein are pharmaceutical compositions comprising immunogenic saccharide-carrier conjugates comprising saccharides from *Haemophilus influenzae* serotypes and methods of administering the pharmaceutical compositions to subject, for example, to reduce or prevent infection with *H. influenzae*. Also provided aherein are methods of inducing an immune response, such as the production of antibodies, involving administering any of the pharmaceutical compositions comprising immunogenic saccharide-carrier conjugates.

Although *H. influenzae* serotype b has long been associated with significant levels of disease in individuals, including young children, the prevelance of disease (as well as asymptomatic carriage) associated with non-b serotypes is on the rise (Campos et al. *Clin. Infect. Dis.* (2003) 37:841-5; Jin et al. *Infect. Immun.* (2007) 75:2650-4; Ladhani et al. *Emerg. Infect. Dis.* (2012) 18:725-32. For example, increasing rates of invasive clinical disease due to *H. influenzae* type a (Hia) have been reported in the Canadian north, as well as in Alaska (USA) and in aboriginal populations in the southwestern USA and Australia and in the general community in Saudi Arabia (Ulanova J. *Vaccines* (2013); Ulanova et al. *Lancet Infectious Diseases*(2014) 14:70-82; Boisvert et. al. *Can. J. Infect. Dis. Med. Microbiol.* (2015) 26:291-2; Whyte et al. *Microb. Dis.* (2015) 3; Roaa et al. *J. Infect. Dev. Ctries*. (2016) 10:528-32; Tsang et al. *Int. J. Circumpolar Health* (2016) 75:29798. Incidence rates of invasive disease in the Canadian circumpolar region have been reported to be as high as 87.5 per 100,000 in children aged under 2 years, (Rotondo et al. *Int. J. Circumpolar Health* (2013) 72:211-42) to 419 per 100,000 in the Keewatin region of Nunavut in children aged under 5 years (McConnell et al. *Pediatr. Infect. Dis. J*. (2007) 26:1025-31. These very rates of serious invasive clinical disease in very young children in these communities has resulted in the increased need for a new vaccine that will reduce those rates of mortality and morbidity associated with this pathogen (Jin et al. *Infect. Immun.* (2007) 75:2650-4; Ulanova J. *Vaccines* (2013)), such that it is considered a public health priority for prevention (Boisvert et. al. *Can. J. Infect. Disea. Med. Microbiol.* (2015) 26:291-2). Emerging serious clinical has also been reported caused by other *H. influenzae* serotypes, including types d, e, and f in Australia, Spain, England and Wales (Campos et al. *Clin. Infect. Dis.* (2003) 37:841-5; Warren et al. *J. Med. Microbiol.* (2010) 59:370-2; Ladhani et al. *Emerg. Infect. Dis.* (2012) 18:725-32; Su et al. *BMC Genomics* (2014) 15:38).

The immunogenic saccharide-carrier conjugates described herein and pharmaceutical compositions thereof may be effective in reducing or preventing infection with *H. influenzae*. Indeed, it was recently demonstrated that administration of saccharide-polypeptide conjugates comprising saccharides from *H. influenzae* serotype a were effective in generating antibodies to the saccharides that were capable of bacteriocidal activity. See, Cox et al. *Vaccine* (2017) 35: 6129-6136.

Provided herein is a brief summary. This summary can be used to provide an understanding of embodiments provided herein, but the embodiments are not limited to what is provided in this summary.

Provided herein is a pharmaceutical composition comprising an immunogenic saccharide-polypeptide conjugate comprising a *Haemophilus influenzae* serotype a capsular polysaccharide, fragment thereof, or combination thereof conjugated to a polypeptide, wherein the immunogenic saccharide-polypeptide conjugate has a molecular weight from approximately 50 kDa to approximately 12,500 kDa, a ratio (w/w) of capsular polysaccharide to polypeptide from 0.2 to 5, or a combination thereof.

Provided herein is a pharmaceutical composition comprising an immunogenic saccharide-polypeptide conjugate comprising a *Haemophilus influenzae* serotype c capsular polysaccharide, fragment thereof, or combination thereof conjugated to a polypeptide, wherein the immunogenic saccharide-polypeptide conjugate has a molecular weight from approximately 50 kDa to approximately 12,500 kDa, a ratio (w/w) of capsular polysaccharide to polypeptide from 0.2 to 5, or a combination thereof.

Provided herein is a pharmaceutical composition comprising an immunogenic saccharide-polypeptide conjugate comprising a *Haemophilus influenzae* serotype d capsular polysaccharide, fragment thereof, or combination thereof conjugated to a polypeptide, wherein the immunogenic saccharide-polypeptide conjugate has a molecular weight from approximately 50 kDa to approximately 12,500 kDa, a ratio (w/w) of capsular polysaccharide to polypeptide from approximately 0.2 to approximately 5, or a combination thereof.

Provided herein is a pharmaceutical composition comprising an immunogenic saccharide-polypeptide conjugate comprising a *Haemophilus influenzae* serotype e capsular polysaccharide, fragment thereof, or combination thereof conjugated to a polypeptide, wherein the immunogenic saccharide-polypeptide conjugate has a molecular weight from approximately 50 kDa to approximately 12,500 kDa, a ratio (w/w) of capsular polysaccharide to polypeptide from 0.2 to 5, or a combination thereof.

Provided herein is a pharmaceutical composition comprising an immunogenic saccharide-polypeptide conjugate comprising a *Haemophilus influenzae* serotype f capsular polysaccharide, fragment thereof, or combination thereof conjugated to a polypeptide, wherein the immunogenic saccharide-polypeptide conjugate has a molecular weight from approximately 50 kDa to approximately 12,500 kDa, a ratio (w/w) of capsular polysaccharide to polypeptide from approximately 0.2 to approximately 5, or a combination thereof.

Provided herein is a pharmaceutical composition comprising an immunogenic saccharide-polypeptide conjugate comprising a capsular polysaccharide, fragment thereof, or combination thereof selected from the group consisting of serotype c, d, e, and f of *Haemophilus influenzae* conjugated to a polypeptide.

Provided herein is a pharmaceutical composition comprising a plurality of immunogenic saccharide-polypeptide conjugates each comprising individually a capsular polysaccharide, fragment thereof, or combination thereof from serotype c, d, e, or f of *Haemophilus influenzae*; each conjugated to a polypeptide.

Provided herein is a pharmaceutical composition comprising a plurality of at least two unique immunogenic saccharide-polypeptide conjugates each comprising individually a capsular polysaccharide, fragment thereof, or combination thereof from a unique serotype selected from the group consisting of a, b, c, d, e, and f of *Haemophilus influenzae*; each conjugated to a polypeptide.

Any of the pharmaceutical compositions described herein may further comprise one or more adjuvant and/or excipient.

Provided herein is a method comprising administering to a subject a first composition, wherein the first composition is one of any pharmaceutical compositions described herein.

Provided herein is a method of making a composition comprising contacting one of any immunogenic saccharide-polypeptide conjugates described herein with an excipient, an adjuvant, or any combination thereof.

Provided herein is a method of eliciting an immunoprotective antibody response to one of any saccharide-polypeptide conjugates described herein, or any fragment thereof.

A kit comprising of one of any pharmaceutical compositions described herein contained in a container. In some embodiments, the kit comprises one or more doses of any of the pharmaceutical compositions described herein.

Provided herein is a pharmaceutical composition comprising an immunogenic saccharide-glycosphingolipid conjugate comprising a *Haemophilus influenzae* serotype a capsular polysaccharide, fragment thereof, or combination thereof conjugated to a glycosphingolipid, wherein the immunogenic saccharide-glycosphingolipid conjugate has a molecular weight from approximately 25 kDa to approximately 12,500 kDa, a ratio (w/w) of capsular polysaccharide to glycosphingolipid from approximately 5 to approximately 24,000, or a combination thereof.

Provided herein is a pharmaceutical composition comprising an immunogenic saccharide-glycosphingolipid conjugate comprising a *Haemophilus influenzae* serotype b capsular polysaccharide, fragment thereof, or combination thereof conjugated to a glycosphingolipid, wherein the immunogenic saccharide-glycosphingolipid conjugate has a molecular weight from approximately 25 kDa to approximately 12,500 kDa, a ratio (w/w) of capsular polysaccharide to glycosphingolipid from approximately 5 to approximately 24,000, or a combination thereof.

Provided herein is a pharmaceutical composition comprising an immunogenic saccharide-glycosphingolipid conjugate comprising a *Haemophilus influenzae* serotype c capsular polysaccharide, fragment thereof, or combination thereof conjugated to a glycosphingolipid, wherein the immunogenic saccharide-glycosphingolipid conjugate has a molecular weight from approximately 25 kDa to approximately 12,500 kDa, a ratio (w/w) of capsular polysaccharide to glycosphingolipid from approximately 5 to approximately 24,000, or a combination thereof.

Provided herein is a pharmaceutical composition comprising an immunogenic saccharide-glycosphingolipid conjugate comprising a *Haemophilus influenzae* serotype d capsular polysaccharide, fragment thereof, or combination thereof conjugated to a glycosphingolipid, wherein the immunogenic saccharide-glycosphingolipid conjugate has a molecular weight from approximately 25 kDa to approximately 12,500 kDa, a ratio (w/w) of capsular polysaccharide to glycosphingolipid from approximately 5 to approximately 24,000, or a combination thereof.

Provided herein is a pharmaceutical composition comprising an immunogenic saccharide-glycosphingolipid conjugate comprising a *Haemophilus influenzae* serotype e capsular polysaccharide, fragment thereof, or combination thereof conjugated to a glycosphingolipid, wherein the immunogenic saccharide-glycosphingolipid conjugate has a molecular weight from approximately 25 kDa to approximately 12,500 kDa, a ratio (w/w) of capsular polysaccharide to glycosphingolipid from approximately 5 to approximately 24,000, or a combination thereof.

Provided herein is a pharmaceutical composition comprising an immunogenic saccharide-glycosphingolipid conjugate comprising a *Haemophilus influenzae* serotype f capsular polysaccharide, fragment thereof, or combination thereof conjugated to glycosphingolipid, wherein the immunogenic saccharide-polypeptide conjugate has a molecular weight from approximately 25 kDa to approximately 12,500 kDa, a ratio (w/w) of capsular polysaccharide to glycosphingolipid from 5 to 24,000, or a combination thereof.

Provided herein is a pharmaceutical composition comprising an immunogenic saccharide-glycosphingolipid conjugate comprising a capsular polysaccharide, fragment thereof, or combination thereof selected from the group consisting of serotype a, b, c, d, e, and f of *Haemophilus influenzae* conjugated to a glycosphingolipid.

Provided herein is a pharmaceutical composition comprising a plurality of immunogenic saccharide-glycosphingolipid conjugates each comprising individually a capsular polysaccharide, fragment thereof, or combination thereof from serotype a, b, c, d, e, or f of *Haemophilus influenzae*; each conjugated to a glycosphingolipid.

Provided herein is a pharmaceutical composition comprising a plurality of at least two unique immunogenic saccharide-glycosphingolipid conjugates each comprising individually a capsular polysaccharide, fragment thereof, or combination thereof from a unique serotype selected from the group consisting of a, b, c, d, e, and f of *Haemophilus influenzae*; each conjugated to a glycosphingolipid.

Any of the pharmaceutical compositions described herein may further comprise one or more adjuvant and/or excipient.

Provided herein is a method of eliciting an immunoprotective antibody response to one of any saccharide-polypeptide conjugates described herein, or any fragment thereof.

Provided herein is a method comprising administering to a subject a first composition, wherein the first composition is one of any pharmaceutical compositions described herein. In some embodiments, the method further comprises administering to the subject a second composition, wherein the first composition is one of any pharmaceutical compositions described herein.

Provided herein is a method of making a composition comprising contacting one of any the immunogenic saccharide-glycosphingolipid conjugates described herein with an excipient, an adjuvant, or any combination thereof.

Provided herein is a kit comprising any one of the pharmaceutical compositions described herein contained in a container. In some embodiments, the kit comprises one or more doses of any of the pharmaceutical compositions described herein.

Provided herein is a pharmaceutical composition comprising an immunogenic saccharide-lipid conjugate comprising a *Haemophilus influenzae* serotype a capsular polysaccharide, fragment thereof, or combination thereof conjugated to a lipid, wherein the immunogenic saccharide-lipid conjugate has a molecular weight from approximately 25 kDa to approximately 12,500 kDa, a ratio (w/w) of capsular polysaccharide to lipid from approximately 5 to approximately 24,000, or a combination thereof.

A pharmaceutical composition comprising an immunogenic saccharide-lipid conjugate comprising a *Haemophilus influenzae* serotype b capsular polysaccharide, fragment thereof, or combination thereof conjugated to a lipid, wherein the immunogenic saccharide-lipid conjugate has a molecular weight from approximately 25 kDa to approximately 12,500 kDa, a ratio (w/w) of capsular polysaccharide to lipid from approximately 5 to approximately 24,000, or a combination thereof.

Provided herein is a pharmaceutical composition comprising an immunogenic saccharide-lipid conjugate comprising a *Haemophilus influenzae* serotype c capsular polysaccharide, fragment thereof, or combination thereof conjugated to a lipid, wherein the immunogenic saccharide-lipid conjugate has a molecular weight from approximately 25 kDa to approximately 12,500 kDa, a ratio (w/w) of capsular polysaccharide to polypeptide from approximately 5 to approximately 24,000, or a combination thereof.

Provided herein is a pharmaceutical composition comprising an immunogenic saccharide-lipid conjugate comprising a *Haemophilus influenzae* serotype d capsular polysaccharide, fragment thereof, or combination thereof conjugated to a lipid, wherein the immunogenic saccharide-lipid conjugate has a molecular weight from approximately 25 kDa to approximately 12,500 kDa, a ratio (w/w) of capsular polysaccharide to lipid from approximately 5 to approximately 24,000, or a combination thereof.

Provided herein is a pharmaceutical composition comprising an immunogenic saccharide-lipid conjugate comprising a *Haemophilus influenzae* serotype e capsular polysaccharide, fragment thereof, or combination thereof conjugated to a lipid, wherein the immunogenic saccharide-lipid conjugate has a molecular weight from approximately 25 kDa to approximately 12,500 kDa, a ratio (w/w) of capsular polysaccharide to lipid from approximately 5 to approximately 24,000, or a combination thereof.

Provided herein is a pharmaceutical composition comprising an immunogenic saccharide-lipid conjugate comprising a *Haemophilus influenzae* serotype f capsular polysaccharide, fragment thereof, or combination thereof conjugated to lipid, wherein the immunogenic saccharide-lipid conjugate has a molecular weight from approximately 25 kDa to approximately 12,500 kDa, a ratio (w/w) of capsular polysaccharide to lipid from approximately 5 to approximately 24,000, or a combination thereof.

Provided herein is a pharmaceutical composition comprising an immunogenic saccharide-lipid conjugate comprising a capsular polysaccharide, fragment thereof, or combination thereof selected from the group consisting of serotype a, b, c, d, e, and f of *Haemophilus influenzae* conjugated to a lipid.

Provided herein is a pharmaceutical composition comprising a plurality of immunogenic saccharide-lipid conjugates each comprising individually a capsular polysaccharide, fragment thereof, or combination thereof from serotype a, b, c, d, e, or f of *Haemophilus influenzae*; each conjugated to a lipid.

Provided herein is a pharmaceutical composition comprising a plurality of at least two unique immunogenic saccharide-lipid conjugates each comprising individually a capsular polysaccharide, fragment thereof, or combination thereof from a unique serotype selected from the group consisting of a, b, c, d, e, and f of *Haemophilus influenzae*; each conjugated to a lipid.

Any of the pharmaceutical compositions described herein may further comprise one or more adjuvant and/or excipient.

Provided herein is a method of eliciting an immunoprotective antibody response to one of any saccharide-lipid conjugates described herein, or any fragment thereof.

Provided herein is a method comprising administering to a subject a first composition, wherein the first composition is any one of the pharmaceutical compositions described herein.

Provided herein is a method of making a composition comprising contacting any one of the immunogenic saccharide-lipid conjugates described herein with an excipient, an adjuvant, or any combination thereof.

Provided herein is a kit comprising of any one of the pharmaceutical compositions described herein contained in a container. In some embodiments, the kit comprises one or more doses of any of the pharmaceutical compositions described herein.

These and other aspects of the invention, as well as various embodiments, thereof, will become more apparent in reference to the detailed description of the invention.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Several aspects are described below with reference to example applications for illustration. It should be understood that numerous specific details, relationships, and methods are set forth to provide a full understanding of the features described herein. One having ordinary skill in the relevant art, however, will readily recognizes that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range covering plus or minus up to 20%, up to 10%, up to 5%, or up to 1% of a given value. Where particular values are described in the application and claims, unless otherwise stated the term "about" can mean within an acceptable error range for the particular value should be assumed.

A "unit dose" when used in reference to a pharmaceutical composition can refer to units suitable as unitary dosage for humans, each unit containing a predetermined quantity of active material calculated to produce the desired therapeutic effect. In some instance the unit dose can contain a diluent; i.e., carrier, or vehicle. In some instances the unit dose can be a physically discrete.

A "carbohydrate," "saccharide," "sugar," or "starch" is a molecule comprised of carbon, hydrogen, and oxygen atoms. The term carbohydrate refers to all carbohydrate, saccharide, sugar, or starch molecules of any size, structure, or function. A carbohydrate can be a monosaccharide or a single sugar molecule. Two or more monosaccharides may be joined by one or more glycosidic bonds to produce higher order carbohydrates. A disaccharide is a carbohydrate comprised of two monosaccharides, an oligosaccharide is comprised of about 3 to about 10 monosaccharides, and a polysaccharide is comprised of about 10 or more monosaccharides. In certain embodiments, the carbohydrate is lactose, maltodextrin, corn syrup, corn syrup solids, and any combination thereof. In certain embodiments, the carbohydrate is lactose, maltodextrin, or any combination thereof.

The term "saccharide" can refer to a saccharide, oligosaccharide or polysaccharide. For example, saccharide can mean a monosaccharide, a disaccharide, a trisaccharide, a tetrasaccharide, a pentasaccharide, a hexasaccharide, a heptasaccharide, an octasaccharide, a nonasaccharide, or a decasaccharide. An oligosaccharide can refer to two to ten saccharides. A polysaccharide can refer to more than ten saccharides. In some embodiments, the saccharide is a a glucose, galacose, ribose, ribitol, mannose, N-acetylglucosamine, N-acetyle-D-mannosamine, or N-acetylgalactosamine. n some embodiments, the oligosaccharide or polysaccharide comprises at least one glucose, galacose, ribose, ribitol, mannose, N-acetylglucosamine, N-acetyl-D-mannosamine, or N-acetylgalactosamine.

The term "polypeptide" can refer to a single linear chain of amino acids held together by amide bonds. A polypeptide can refer to at least two amino acids. A polypeptide can be an oligopeptide, wherein the term "oligopeptide" can refer to a single chain of from two to twenty amino acids joined by amide bonds. A polypeptide can be a protein, wherein the term "protein" can refer to a single chain of fifty or more amino acids held together by amide bonds.

The term "carrier" can refer to any polypeptide or lipid that can induce an immune response.

In general, a "lipid" is comprised of three fatty acid chains connected to a glycerol molecule through an ester bond. The term lipid refers to all lipid molecules of any size, structure, or function. Typically, a lipid is a hydrophobic molecule that is insoluble in water. In some embodiments, the term "lipid" can refer to any lipid that can elicit an immune response. In some embodiments, the lipid is a glycosphingolipid. In some embodiments, the lipid is α-galactosylceramide or other agelasphin derivative.

The term "glycosphingolipid" can refer to any glycosphingolipid that can elicit an immune response. A glycosphingolipid can be α-galactosylceramide or other agelasphin derivative.

The term an "immune response" can refer to the production of cytokines and/or antibodies with a degree of specificity for an antigen after administering the antigen to a subject. In some instances, the term "immune response" can refer to any change in immune cells or change caused by immune cells after administering the antigen to a subject. An immune response can be T cell independent, T cell dependent, or both. A saccharide can be "immunogenic" if it can elicit an immune response. A carrier can be "immunogenic" if it can elicit an immune response. A polypeptide can be "immunogenic" if it can elicit an immune response. A glycosphingolipid can be "immunogenic" if it can elicit an immune response. A lipid can be "immunogenic" if it can elicit an immune response. A saccharide-polypeptide conjugate can be "immunogenic" if it can elicit an immune response. A saccharide-carrier conjugate can be "immunogenic" if it can elicit an immune response. A saccharide-glycosphingolipid conjugate can be "immunogenic" if it can elicit an immune response. A saccharide-lipid conjugate can be "immunogenic" if it can elicit an immune response.

In some embodiments, a saccharide-carrier conjugate is to determine to be immunogenic if antibodies specific to the *H. influenzae* saccharides are detected in the subject, e.g., a biological sample (e.g., serum) from the subject. In some embodiments, a saccharide-carrier conjugate is to determine to be immunogenic if enhanced levels of antibodies specific to the *H. influenzae* saccharides are detected in the subject, e.g., a biological sample (e.g., serum) from the subject. In some embodiments, a saccharide-carrier conjugate is to determine to be immunogenic if functional antibodies specific to the *H. influenzae* saccharides (e.g., antibodies having bacteriocidal activity, opsonophagocytic activity) are detected in the subject, e.g., a biological sample (e.g., serum) from the subject. In some embodiments, enhanced levels of functional antibodies specific to the *H. influenzae* saccharides are detected in the subject.

The antibodies specific to the *H. influenzae* saccharides may be of any antibody isotype (e.g., IgA, IgG, IgM, IgE, IgD), or a combination thereof. In some embodiments, the antibodies specific to the *H. influenzae* saccharides are IgG antibodies. In some embodiments, the antibodies specific to the *H. influenzae* saccharides are IgG1, IgG2, IgG3, or IgG4 antibodies or a combination thereof.

As used herein, an antibody that is specific to the *H. influenzae* saccharides recognizes (binds to) saccharides from *H. influenzae*, e.g., capsular saccharides. In some embodiments, the antibodies that are specific to *H. influenzae* saccharides recognizes (binds to) saccharides from a specific *H. influenza* serotype. In some embodiments, the antibodies that are specific to *H. influenzae* saccharides recognizes (binds to) saccharides from *H. influenza* serotype a. In some embodiments, the antibodies that are specific to *H. influenzae* saccharides recognizes (binds to) saccharides from *H. influenza* serotype b. In some embodiments, the antibodies that are specific to *H. influenzae* saccharides recognizes (binds to) saccharides from *H. influenza* serotype c. In some embodiments, the antibodies that are specific to *H. influenzae* saccharides recognizes (binds to) saccharides from *H. influenza* serotype d. In some embodiments, the antibodies that are specific to *H. influenzae* saccharides recognizes (binds to) saccharides from *H. influenza* serotype e. In some embodiments, the antibodies that are specific to *H. influenzae* saccharides recognizes (binds to) saccharides from *H. influenza* serotype f. In some embodiments, the antibodies that are specific to *H. influenzae* saccharides recognizes (binds to) saccharides from more than one *H. influenzae* serotype (e.g., more than one serotype selected from a, b, c, d, e, f). Antibodies that recognize (bind to) saccharides from more than one *H. influenzae* serotype may be referred to as cross reactive antibodies.

The term "homology" can mean percent sequence identity between a particular nucleic acid or amino acid sequence and another nucleic acid or amino acid sequence. First, a nucleic acid or amino acid sequence can be compared another sequence using the BLAST 2 Sequences (Bl2seq) program from the stand-alone version of BLASTZ containing BLASTN version 2.0.14 and BLASTP version 2.0.14. BLASTN can be used to compare nucleic acid sequences, while BLASTP can be used to compare amino acid sequences. Once aligned, the number of matches is determined by counting the number of positions where an identical nucleotide or amino acid residue is presented in both sequences. The percent sequence identity or homology can be determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100%.

The term "length homology" can mean percent length identity between the length of a particular polypeptide and the length of another polypeptide. "Length homology" can in some instances be calculated by dividing the number of amino acids in a first peptide chain by the number of amino acids in a second peptide chain and multiplying the result by 100%. Chain amino acids can be those forming the backbone of the peptide.

The term "length" in reference to a polypeptide can refer to counting the number of amino acids along the amino acid chain.

The term "immunogenic fragment" can be a fragment that is conjugated to a polypeptide, glycosphingolipid, or lipid, administered to a subject, and which elicits an immune response. In some instances, the fragment can be a fragment of a capsular polysaccharide. In other instances, the polypeptide can be $CRM_{197}$. In some instances, the glycosphingolipid can be α-galactosylceramide. In some instances, the lipid can be α-galactosylceramide.

Immunogenic, which can but need not be obligated to be preceded any term herein, can mean that which, when administered to a subject, which can be a human or any other animal, for example, a dog, cat, rat, mouse, sheep, or monkey, produces an immune response in the animal. For example, a dog can be *Canis lupis familiarius*, a cat can be *Felis catus*, a rat can be *Rattus norvegicus*, a mouse can be *Mus musculus*, a sheep can be *Ovis aries*, or a monkey can be *Simia inuus*. The administration can be, for example, subcutaneous, intramuscular, or rectal, for example in the form of a suppository.

In some embodiments, a unique immunogenic saccharide-polypeptide conjugate can be one that differs from other unique immunogenic saccharide-polypeptide conjugates, for example in a plurality of these, by at least one aspect. For example, the unique immunogenic saccharide-polypeptide conjugate can differ by the saccharide or fragment thereof it contains—in that this can render the unique immunogenic saccharide-polypeptide conjugate unique, or by the polypeptide it contains, or both. In some instances, unique immunogenic saccharide-polypeptide conjugates, to be unique, simply need not be 100% identical. In some instances, the unique immunogenic saccharide-polypeptide conjugate can be in free base (deprotonated) form, or salt form.

In some embodiments, a unique immunogenic saccharide-glycosphingolipid conjugate can be one that differs from other unique immunogenic saccharide-glycosphingolipid conjugates, for example, in a plurality of these, by at least one aspect. For example, the unique immunogenic saccharide-glycosphingolipid conjugate can differ by the saccharide or fragment thereof it contains—in that this can render the unique immunogenic saccharide-glycosphingolipid conjugate unique, or by the glycosphingolipid it contains, or both. In some instances, unique immunogenic saccharide-glycosphingolipid conjugates, to be unique, simply need not be 100% identical. A glycosphingolipid can be α-galactosylceramide. In some instances, the unique immunogenic saccharide-glycosphingolipid conjugate can be in free base (deprotonated) form, or salt form.

In some embodiments, a unique immunogenic saccharide-lipid conjugate can be one that differs from other unique immunogenic saccharide-lipid conjugates, for example, in a plurality of these, by at least one aspect. For example, the unique immunogenic saccharide-lipid conjugate can differ by the saccharide or fragment thereof it contains—in that this can render the unique immunogenic saccharide-lipid conjugate unique, or by the lipid it contains, or both. In some instances, unique immunogenic saccharide-lipid conjugates, to be unique, simply need not be 100% identical. A lipid can be a glycosphingolipid. A lipid can be α-galactosylceramide. In some instances, the unique immunogenic saccharide-lipid conjugate can be in free base (deprotonated) form, or salt form.

The terms "opsonophagocytosis" or "opsonophagocytic activity" refer to binding of antibodies to a molecule, such as a bacterium, and promoting its phagocytosis. In general, opsonophagocytic activity of antibodies or a sample containing antibodies (e.g., a biological sample from a subject) can be assessed using an opsonophagocytosis assay. See, e.g., Dwyer et al. *Methods Mol. Biol.* (2014) 1100:373-9.

The term "partly mitigated" in reference to the toxin activity of a polypeptide can refer to a decreased toxicity of the polypeptide as compared to a wild type version of the polypeptide.

The term "molecular weight" can be a number average molecular weight or a weight average molecular weight.

The term "plurality" can mean two or more.

A "subject" as used herein, refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject can be a subject in need thereof.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

Bacteria and fungi can incorporate saccharides into their surface structure, such as a capsule. For example, *Haemophilus influenzae* (*H. influenzae*) can contain saccharides in its surface structure. Capsular saccharide structures have been shown to be important determinants of virulence for *H. influenzae*, and antibodies directed to those capsules confer protection against disease by initiating opsonization and complement-dependent bacteriolysis (see, e.g., U.S. Pat. No. 4,644,059; Swift et al. *Microb. Pathogen.* (1991) 10:261-9; Nix et al. (2015) *Emerg. Infect. Dis.* (2015) 21:273-9; Konini et al. *Prevent Med. Rep.* (2016) 3:145-50). The saccharides can be antigens that can induce an immune response in host, such as an animal or human. For example, B cells can produce antibodies against a saccharide. This response can be a T cell independent immune response. An immune response can be induced with full-length, native form polysaccharides, oligosaccharides, or fragments thereof. An immune response can be induced with full-length, native form capsular polysaccharides, or fragments thereof. The saccharides present in the capsule of *H. influenzae* can be used to classify the bacteria into a subclass or serotype of *H. influenzae* strains. In general, a serotype can refer to the type of a microorganism determined by its constituent antigens. The constituent antigens can be different saccharides, such as different capsular polysaccharides or immunogenic fragments thereof. Non-limiting examples of *H. influenzae* serotypes can include serotype a, serotype b, serotype c, serotype d, serotype e, or serotype f (see, Table 1), referred to as "Hia", "Hib", "Hic", "Hid", "Hie", or "Hif", respectively As used herein, an "immunogenic fragment" of a capsular polysaccharide refers to any fragment (portion) of a capsular polysaccharide that may stimulate an immune response or to which an immune response may be directed. In some embodiments, an immune response directed towards an immunogenic fragment of a capsular polysaccharide may provide a protective effect against infection. Immunogenic fragments of a capsular polysaccharide may be identified using methods known in the art, for example, for example by fractionating capsular polysaccharides and screening for immunogenic fragments. In some embodiments, the capsular polysaccharides are fragmented to achieve fragments of a desired size.

In some embodiments, the polysaccharides may be subjected to fragmentation to achieve a desired size of fragments. The size of the fragments may be assessed, for example, as the degree of polymerization. As used herein, the term "degree of polymerization" refers to the number of monomers in a polymer, such as the number of saccharides in a polysaccharide. In some embodiments, fragmentation of polysaccharides is performed to achieve an average degree of polymerization (DP) in the oligosaccharide of less than 30. In some embodiments, the average degree of polymerization (DP) in the oligosaccharide is less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more. The degree of polymerization may measured, for example, by ion exchange chromatography and/or by colorimetric assays. In some emboidments, fragments above and/or below a desired size may be removed from a population of oligosaccharides.

The identification of an immunogenic fragment may be identified, for example, by NMR analysis.

Covalent linking of an antigenic molecules (e.g., saccharide) to a carrier may confer enhanced immunogenicity and T-cell dependence to the antigenic molecule (Pozsgay et al. (1999) *PNAS*, 96:5194-97; Lee et al. (1976) *J. Immunol.*, 116:1711-18; Dintzis et al. (1976) *PNAS*, 73:3671-75). By conjugating a saccharide to a carrier, the immune response to the saccharide can be enhanced via linked recognition. Linked recognition can result in B cell activation as a result of the B cell recognizing the saccharide of the saccharide-carrier conjugate, internalizing the saccharide-carrier conjugate, and then presenting the carrier via a Major Histocompatibility Complex (MHC) such as MHC class I, or a non-classical MHC such as CD1d. The presentation of the carrier can then elicit T cell activation or invariant Natural Killer T cell (iNKT cell) activation, which can then result in activation of the B cell that recognized the saccharide and subsequent production of saccharide-specific antibodies by that B cell.

As an example, a saccharide conjugated to a polypeptide can enhance an immune response to the saccharide by inducing a T cell dependent response. A saccharide alone may not stimulate T cells because, for example, a saccharide may not be loaded onto the MHC of antigen presenting cells. It is generally thought that saccharide antigens stimulate a T cell-independent B cells response. However, peptides can be loaded onto MHC, recognized by the T cell, and stimulate a T cell response Therefore, by conjugating a saccharide to a polypeptide a T cell-dependent response may be stimulated. In some instances, the saccharide-polypeptide conjugate can be loaded on the MHC, recognized by the T cell and stimulate a T cell response. T cells can then stimulate a more vigorous immune response and also promote a more rapid and long-lasting immunologic memory.

Provided herein are saccharide-carrier conjugates that can be used to induce an immune response in a subject. They are also referred to as immunogenic saccharide-carrier conjugates.

Provided herein are saccharide-polypeptide conjugates that can be used to induce an immune response, which can be referred to as immunogenic saccharide-polypeptide conjugates. In some instances, the immunogenic saccharide-polypeptide conjugates can provide immune protection against a saccharide or organism containing the saccharides. In other instances, the immunogenic saccharide-polypeptide conjugates can be part of a vaccine. As another example, a saccharide conjugated to a glycosphingolipid or lipid can enhance an immune response to the saccharide by inducing an iNKT cell dependent response. A saccharide alone may not stimulate iNKT cells because, for example, a saccharide may not be loaded onto CD1d of antigen presenting cells. However, a glycosphingolipid or lipid, such as α-galactosylceramide, can be loaded onto CD1d. Therefore, by conjugating a saccharide to a glycosphingolipid or lipid, the glycosphingolipid or lipid can then be loaded onto the CD1d, recognized by the iNKT cell, and stimulate an iNKT cell response. iNKT cells can then stimulate a more vigorous immune response and also promote a more rapid and long-lasting immunologic memory.

Provided herein are saccharide-glycosphingolipid conjugates or saccharide-lipid conjugates that can be used to induce an immune response, which can be referred to as immunogenic saccharide-glycosphingolipid conjugates or immunogenic saccharide-lipid conjugates, respectively. In some instances, the immunogenic saccharide-glycosphingolipid conjugates or immunogenic saccharide-lipid conjugates can provide immune protection against a saccharide or organism containing the saccharides. In other instances, the immunogenic saccharide-glycolipid conjugates or immunogenic saccharide-lipid conjugates can be part of a vaccine.

H. influenzae Saccharide-Carrier Conjugates

Provided herein are compositions comprising immunogenic saccharide-polypeptide conjugates comprising saccharides from H. influenzae, also referred to as immunogenic saccharide-carrier conjugate compositions. A saccharide-carrier conjugate and/or saccharide-carrier conjugate composition may be considered immunogenic if the saccharide-carrier conjugate or saccharide-carrier conjugate composition induces enhanced levels of H. influenzae-specific antibodies and higher antibody function (e.g., bacteriocidal activity, opsonophagocytic activity). In some embodiments, the saccharide-carrier conjugate and/or saccharide-carrier conjugate composition may be considered immunogenic if the saccharide-carrier conjugate or saccharide-carrier conjugate composition induces enhanced levels of H. influenzae-specific IgG antibodies and higher antibody function (e.g., bacteriocidal activity, opsonophagocytic activity).

In some embodiments, an immunogenic saccharide-carrier conjugate composition is a saccharide conjugated to a carrier. In some embodiments, the carrier is a polypeptide, a glycosphingolipid, or a lipid. In some embodiments, the immunogenic saccharide-polypeptide conjugate composition is a saccharide conjugated to a polypeptide. In some embodiments, the immunogenic saccharide-polypeptide conjugate composition is a capsular polysaccharide conjugated to a polypeptide. In some embodiments, the immunogenic saccharide-polypeptide conjugate composition is a capsular polysaccharide or fragment of the capsular polysaccharide conjugated to a polypeptide. In some embodiments, the immunogenic saccharide-polypeptide conjugate comprises a saccharide antigen coupled to one or more polypeptides.

A saccharide antigen can elicit an immune response. In some embodiments, an immune response to a saccharide antigen is stimulated or enhanced if the saccharide antigen is conjugated to a polypeptide, such as in an immunogenic saccharide-polypeptide conjugate.

In some embodiments, an immunogenic saccharide-glycosphingolipid conjugate composition can be a saccharide conjugated to a glycosphingolipid. In some embodiments, the immunogenic saccharide-glycosphingolipid conjugate composition can be a capsular polysaccharide conjugated to a glycosphingolipid. In some embodiments, the immunogenic saccharide-glycosphingolipid conjugate composition can be a capsular polysaccharide or fragment of the capsular polysaccharide conjugated to a glycosphingolipid. In some embodiments, the immunogenic saccharide-glycosphingolipid conjugate can comprise a saccharide antigen coupled to one or more glycosphingolipids. In some embodiments, the immunogenic saccharide-lipid conjugate composition can be a saccharide conjugated to a lipid.

In some embodiments, the immunogenic saccharide-lipid conjugate composition can be a capsular polysaccharide conjugated to a lipid. In some embodiments, the immunogenic saccharide-lipid conjugate composition can be a capsular polysaccharide or fragment of the capsular polysaccharide conjugated to a lipid. In some embodiments, the immunogenic saccharide-lipid conjugate can comprise a saccharide antigen coupled to one or more lipids.

In some embodiments, the saccharide can be from H. influenzae. H. influenzae can incorporate saccharides into its surface structure (e.g., capsule). In some embodiments, the saccharide is a H. influenzae capsular saccharide. A saccharide can be a full-length, native form polysaccharide, oligosaccharide, or fragments thereof. An oligosaccharide can be a repeating disaccharide unit. A saccharide can be in any form that induces an immune response. The term saccharide encompasses full length saccharides as well as fragments of saccharides. In some embodiments, the saccharide is a capsular polysaccharide or fragment thereof. In some embodiments, the saccharide is a capsular polysaccharide fragment that may be selected based on one or more factors, such as the length of the fragment and/or an immune response elicited by the fragment.

In some embodiments, the capsular polysaccharide is a polyribosyliribitol phosphate capsular polysaccharide. In some embodiments, the saccharide is from a subclass or serotype of H. influenzae. H. influenzae serotypes include serotype a, serotype b, serotype c, serotype d, serotype e, or serotype f. In some embodiments, the saccharides are capsular polysaccharides obtained from H. influenza serotype a (referred to as serotype a saccharides).

A serotype can be one type of oligosaccharide, in which the serotype can consist of oligosaccharides with one type of R group attached as indicated in Table 1. See, Sutton et al. Infect. and Immun. (1982) 35: 95-104, and Aubrey et al. Methods in Mol. Med.(2003) 71:29-50. Alternatively, a serotype can be a mixture of oligosaccharides, in which the oligosaccharides can have different R groups attached as indicated in the examples in Table 1. See, e.g., Jin et al. Infect. Immun. (2007) 75(6): 2650-2654. Table 1 shows exemplary H. influenzae oligosaccharide serotypes. In Table 1, the number indicates the number of the carbon in the structure in which the R group can be attached. For example, for serotype c, the R group can be attached at the third carbon atom (3) in the galactose moiety of the disaccharide.

TABLE 1

Exemplary H. influenzae oligosaccharide serotypes

| Serotype | Oligosaccharide |
|---|---|
| a[1,2] | [4)-β-D-Glc-(1→4)-D-ribitol-5-(PO$_4$→]$_n$ |
| b[5] | [3)-β-D-Ribf-(1→1)-D-ribitol-(5-OPO$_3$→]$_n$ |
| c[3,4,5] | [4)-β-D-GlcNAc-(1→3)-α-D-Gal-1-(PO$_4$→]$_n$<br>           3<br>           ↑   R = OAc or H<br>           R |
| d[6,7,8] | [4)-β-D-GlcNAc-(1→3)-β-D-ManANAc-(1→]$_n$<br>           3<br>           ↑   R = serine, threonine, or alanine<br>           R |
| d[5] | [4)-β-D-GlcNAc-(1→3)-β-D-ManANAc-(1→]$_n$<br>                     6<br>R = L-serine or L-threonine or L-alanine   ↑<br>                         R |
| e[7,9] | [3)-β-D-GlcNAc-(1→4)-β-D-ManANAc-(1→]$_n$ |
| e[5] | [3)-β-D-GlcNAc-(1→4)-β-D-ManANAc-(1→]$_n$<br>           3<br>           ↑<br>           2<br>         β-D-fructose |
| f[3,4,7,10] | [3)-β-D-GalNAc-(1→4)-α-D-GalNAc-1-(PO$_4$→]$_n$<br>           3<br>           ↑<br>         OAc |

[1]Branefors-Helander et al. *Carbohydr. Res.* (1977) 56: 197-202.
[2]Byrd et al. *Carbohydr. Res.* (1987) 166: 47-58.
[3]Banefors-Helander et al. *Carbohydr. Res.* (1979) 76: 197-202.
[4]Egan et al. Carbohydr. Res. (1980) 80: 305-16.
[5]Sutton et al. Infect. Immun. (1982) 35: 95-104.
[6]Branefors-Helander et al. *Carbohydr. Res.* (1981) 97: 285-91.
[7]Tsui et al. Carbohydr. Res. (1981) 88: 85-92.
[8]Lam et al Res. Microbiol. (2011) 162: 483-7.
[9]Branefors-Helander et al. Carbohydr. Res. (1981): 88: 77-84.
[10]Branefors-Helander et al. Carbohydr. Res. (1980) 79: 308-12.
[11]Yildirim et al. *Eur. J. Biochem.* (2003) 270: 153-67.

In some embodiments, the saccharides are capsular polysaccharides obtained from *H. influenza* serotype b (referred to as serotype b saccharides). In some embodiments, the saccharides are capsular polysaccharides obtained from *H. influenza* serotype c (referred to as serotype c saccharides). In some embodiments, the saccharides are capsular polysaccharides obtained from *H. influenza* serotype d (referred to as serotype d saccharides). In some embodiments, the saccharides are capsular polysaccharides obtained from *H. influenza* serotype e (referred to as serotype e saccharides). In some embodiments, the saccharides are capsular polysaccharides obtained from *H. influenza* serotype f (referred to as serotype f saccharides). In some embodiments, the saccharides are not capsular polysaccharides obtained from *H. influenzae* serotype b.

In some embodiments, the saccharide-carrier conjugates comprise saccharides comprising alternating glucose and ribitol. In some embodiments, the saccharide-carrier conjugates comprise saccharides comprising alternating ribose and ribitol. In some embodiments, the saccharide-carrier conjugates comprise saccharides comprising alternating N-acetylglucosamine and galactose. In some embodiments, the saccharide-carrier conjugates comprise saccharides comprising alternating N-acetylglucosamine and N-acetyl-D-mannosamine. In some embodiments, the saccharide-carrier conjugates comprise saccharides comprising alternating N-acetylglucosamine and N-acetylgalactosamine.

As will be appreciated by one of skill in the art, a strain of *H. influenzae* may produce a capsular polysaccharides of a particular structure. Alternatively, a strain of *H. influenzae* may produce capsular polysaccharides having different structures. For example, as shown in Table 1, saccharides from *H. influenzae* serotype d may contain modifications, such as a serine, threonine, or alanine residue on an N-acetylglucosamine residues or a serine, threonine or alanine residue on N-acetyl-D-mannosamine. In some embodiments, a saccharine containing a particular modification may be isolated from a heterogeneous population of saccharides from a *H. influenzae* serotype.

The saccharides, polysaccharides, or oligosaccharides may be size-reduced. In general, a size-reduced saccharide, polysaccharide, or oligosaccharide may be produced by controlled hydrolysis to generate reducing-end ribose, which can then be reductively animated after purification. In some embodiments, the saccharides, polysaccharides, or oligosaccharides are subjected to sonication to reduce the size of the polymers. See, e.g., Szu et al. *Carbohydro. Res.* (1986) 152: 7-20; and MacNair et al. *Biologicals* (2005)33: 49-58. In some embodiments, saccharide, polysaccharide, or oligosaccharide may be obtained (e.g., from a bacterium or culture thereof) and subsequently size-reduced.

In some embodiments, saccharides, polysaccharides, or oligosaccharides are selected based on a desired size (e.g., molecular weight). In some embodiments, the saccharides, polysaccharides, or oligosaccharides are obtained (e.g., from a bacterium or culture thereof) and analyzed to determine the size(s), and then a population of saccharides, polysaccharides, or oligosaccharides is selected.

In some embodiments, the saccharide is a polysaccharide with a molecular weight of less than 2000 kDa, less than 1500 kDa, less than 1000 kDa, less than 800 kDa, less than 500 kDa, less than 400 kDa, less than 300, less than 200 kDa, less than 100 kDa, less than 50 kDa, or less than 25 kDa. In some embodiments, the saccharide is a *H. influenzae* serotype a polysaccharide and has a molecular weight of less than 2000 kDa, less than 1500 kDa, less than 1000 kDa, less than 800 kDa, less than 500 kDa, less than 400 kDa, less than 300, less than 200 kDa, less than 100 kDa, less than 50 kDa, or less than 25 kDa. In some embodiments, the saccharide is a *H. influenzae* serotype b polysaccharide and has a molecular weight of less than 2000 kDa, less than 1500 kDa, less than 1000 kDa, less than 800 kDa, less than 500 kDa, less than 400 kDa, less than 300, less than 200 kDa, less than 100 kDa, less than 50 kDa, or less than 25 kDa. In some embodiments, the saccharide is a *H. influenzae* serotype c polysaccharide and has a molecular weight of less than 2000 kDa, less than 1500 kDa, less than 1000 kDa, less than 800 kDa, less than 500 kDa, less than 400 kDa, less than 300, less than 200 kDa, less than 100 kDa, less than 50 kDa, or less than 25 kDa. In some embodiments, the saccharide is a *H. influenzae* serotype d polysaccharide and has a molecular weight of less than 2000 kDa, less than 1500 kDa, less than 1000 kDa, less than 800 kDa, less than 500 kDa, less than 400 kDa, less than 300, less than 200 kDa, less than 100 kDa, less than 50 kDa, or less than 25 kDa. In some embodiments, the saccharide is a *H. influenzae* serotype e polysaccharide and has a molecular weight of less than 2000 kDa, less than 1500 kDa, less than 1000 kDa, less than 800 kDa, less than 500 kDa, less than 400 kDa, less than 300, less than 200 kDa, less than 100 kDa, less than 50 kDa, or less than 25 kDa. In some embodiments, the saccharide is a *H. influenzae* serotype f polysaccharide and has a molecular weight of less than 2000 kDa, less than 1500 kDa, less than 1000 kDa, less than 800 kDa, less than 500 kDa, less than 400 kDa, less than 300, less than 200 kDa, less than 100 kDa, less than 50 kDa, or less than 25 kDa.

Without wishing to be bound by any particular theory, it is generally thought that a polysaccharide with a molecular weight of 100 kDa or less may have greater opsonophagocytic activity than a polysaccharide with a molecular weight greater than 100 kDa.

In some embodiments, the saccharide is a polysaccharide with a molecular weight of less than 25 kDa, less than 20 kDa, less than 15 kDa, less than 10 kDa, or less than 5 kDa. In some embodiments, the saccharide is a *H. influenzae* serotype a polysaccharide and has a molecular weight of less than 25 kDa, less than 20 kDa, less than 15 kDa, less than 10 kDa, or less than 5 kDa. In some embodiments, the saccharide is a *H. influenzae* serotype b polysaccharide and has a molecular weight of less than 25 kDa, less than 20 kDa, less than 15 kDa, less than 10 kDa, or less than 5 kDa. In some embodiments, the saccharide is a *H. influenzae* serotype c polysaccharide and has a molecular weight of less than 25 kDa, less than 20 kDa, less than 15 kDa, less than 10 kDa, or less than 5 kDa. In some embodiments, the saccharide is a *H. influenzae* serotype d polysaccharide and has a molecular weight of less than 25 kDa, less than 20 kDa, less than 15 kDa, less than 10 kDa, or less than 5 kDa. In some embodiments, the saccharide is a *H. influenzae* serotype e polysaccharide and has a molecular weight of less than 25 kDa, less than 20 kDa, less than 15 kDa, less than 10 kDa, or less than 5 kDa. In some embodiments, the saccharide is a *H. influenzae* serotype f polysaccharide and has a molecular weight of less than 25 kDa, less than 20 kDa, less than 15 kDa, less than 10 kDa, or less than 5 kDa.

Without wishing to be bound by any particular theory, it is generally thought that an oligosaccharide with a molecular weight of 10 kDa or less may be more immunogenic than an oligosaccharide with a molecular weight greater than 10 kDa. Additionally, an oligosaccharide with a molecular weight of 10 kDa or less may have greater opsonophagocytic activity than an oligosaccharide with a molecular weight greater than 10 kDa.

In general, saccharides can be obtained from or isolated from *H. influenzae*. In some embodiments, saccharides are isolated from *H. influenzae* and then conjugated to a carrier to form a saccharide-carrier conjugate. In some embodiments, saccharides are isolated from *H. influenzae* and then conjugated to a polypeptide to form a saccharide-polypeptide conjugate. In some embodiments, saccharides are isolated from *H. influenzae* and then conjugated to a glycosphingolipid to form a saccharide-glycosphingolipid conjugate. In some embodiments, saccharides are isolated from *H. influenzae* and then conjugated to a lipid to form a saccharide-lipid conjugate.

Any method known in the art for isolating or obtaining unconjugated polysaccharides from bacteria, such as *H. influenza*, may be used. For example, *H. influenzae* (including particular serotypes of *H. influenzae*) may be cultured (e.g., grown in a soy-based medium). The individual polysaccharides can then be purified by steps including centrifugation, precipitation, and ultra-filtration. Example processes for purifying polysaccharides are described, for example, in Albani et al. Carbohydr. Polym. (2015) 116:67-73 and U.S. Pat. Nos. 4,220,717; 4,459,286; and and U.S. Pat. No. 9,782,467 which are incorporated herein by reference.

Alternatively or additionally, polysaccharides may be isolated simultaneously from more than one serotype of *H. influenzae*, which can produce a mixture of polysaccharide serotypes with the desired polysaccharide already combined. For example, more than one serotype of *H. influenzae* may be cultured (e.g., grown in a soy-based medium) separately (in separate cultures) or together in a single culture. The individual polysaccharides can then be purified from each of the cultures or from the single culture and subjected to by steps including centrifugation, precipitation, and/or ultra-filtration. In some embodiments, polysaccharides are obtained from more than one serotype of *H. influenzae* and are then combined (e.g., for conjugation to a carrier).

Furthermore, isolated polysaccharides may be sized by microfluidization. The polysaccharides can be sized, for example, to reduce viscosity in polysaccharide samples and/or to improve filterability for conjugated samples.

A saccharide-polypeptide conjugate can include a saccharide or a fragment thereof which is at least partially embedded in one or more polypeptides. In some embodiments, the one or more polypeptides can have one or more crosslinks. The at least partially embedded saccharide or fragment thereof can, but need not be, covalently bound to at least one of the polypeptides when at least partially embedded therein. The polysaccharide can be prepared as described, for example, in U.S. Pat. No. 4,644,059, which is incorporated herein by reference. The sized polysaccharide can be activated with cyanogen halide, such as bromide, to create an electrophilic group on a polysaccharide. The activated polysaccharide can then be combined with a carrier to create the polysaccharide-carrier conjugate.

In some embodiments, an activated polysaccharide is combined with a polypeptide to produce a polysaccharide-polypeptide conjugate in which hydrazide groups that can be on the polypeptide can react with the activated polysaccharide to form covalent bonds. In some embodiments, an activated polysaccharide is combined with a glycosphingolipid to produce a polysaccharide-glycosphingolipid conjugate, in which hydroxyl groups or oxygen atoms that can be on the glycosphingolipid can react with the activated polysaccharide to form covalent bonds. In some embodiments, an activated polysaccharide is combined with a glycosphingolipid to produce a polysaccharide-glycosphingolipid conjugate, in which hydroxyl groups or oxygen atoms that can be on the sugar moiety of the glycosphingolipid can react with the activated polysaccharide to form covalent bonds. In some embodiments, an activated polysaccharide is combined with a lipid to produce a polysaccharide-lipid conjugate, in which hydroxyl groups or oxygen atoms that can be on the lipid can react with the activated polysaccharide to form covalent bonds. In some embodiments, an activated polysaccharide is combined with a lipid to produce a polysaccharide-lipid conjugate, in which hydroxyl groups or oxygen atoms that can be on a sugar moiety of the lipid can react with the activated polysaccharide to form covalent bonds. In some embodiments, the polysaccharide-carrier conjugate is then be purified by gel permeation chromatography.

In some embodiments, the saccharide is activated or functionalised prior to conjugation. In some emboidments, the saccharide is activated by CDAP (1-cyano-4-dimethyl-amino pyridinium tetrafluoroborate). For example, activation may involve cyanylating reagents, such as CDAP (1-cyano-4-dimethylamino pyridinium tetrafluoroborate).

See, e.g., U.S. Pat. No. 9,248,197, which is incorporated herein by reference. Other examples include carbodiimides, hydrazides, active esters, norborane, p-nitrobenzoic acid, and N-hydroxysuccinimide. In some embodiments, the saccharide is activated by reductive amination. See, e.g., Hsieh Dev. Biol. (1999) 103: 93-104.

A saccharide for use in the saccharide-carrier conjugate, such as a saccharide-polypeptide conjugate, a saccharide-glycosphingolipid conjugate, or saccharide-lipid conjugate, may be obtained from a commercial source. For example, individual H. influenzae polysaccharide serotypes can be obtained in a powder form. These polysaccharides can be dissolved in water and incubated with a salt to dissociate residual impurities, which can then be removed by a filtration step. The purified H. influenzae polysaccharides serotypes can then be conjugated to a polypeptide. In some embodiments, the saccharides can be purified without the use of calcium ions.

In some embodiments, the carrier of an immunogenic saccharide-carrier conjugate is a polypeptide. In some embodiments, the polypeptide of the immunogenic saccharide-polypeptide conjugate is an oligopeptide. In some embodiments, the polypeptide is a carrier protein. In general, the polypeptide can be any polypeptide that allows for conjugation or coupling of saccharide and results in the display of the polypeptide, conjugate, or fragment thereof, or coupling in a way that induces a protective immune response against the saccharide.

A polypeptide can be any polypeptide that allows for conjugation or coupling of a capsular polysaccharide or fragment of the capsular polysaccharide and can result in the display of the conjugate or coupling in a way that can induce a protective immune response against the capsular polysaccharide or fragment of the capsular polysaccharide. Non-limiting examples of polypeptides for use in the immunogenic saccharide-polypeptide include $CRM_{197}$, tetanus toxoid, tetanus toxoid C peptide, a diphtheria toxoid, a cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B streptococcus, a non-typable H. influenzae P4 protein, a non-typable H. influenzae P6 protein, M catarrhalis uspA, a keyhole limpet haemocyanin (KLH), bovine serum albumin (BSA), outer membrane protein complex C, outer membrane protein complex C (OMPC) from N. meningitidis, porins, transferrin binding proteins, the purified protein derivative of tuberculin (PPD), E. coli LT, E. coli ST, exotoxin A from Pseudomonas aeruginosa, and protein D from H. influenzae, or any fragment thereof.

In some embodiments, the polypeptide is a variant of a toxin. As used herein, a variant refers to a polypeptide that may contain one or more modifications (e.g., mutations) relative to a naturally occurring polypeptide. In some embodiments, the one or more modification may reduce or eliminate the toxicity of a toxin. In some embodiments, the variant is an inactive bacterial toxin, such as tetanus toxoid, pertussis toxoid, or cholera toxoid, E. coli LT, E. coli ST, and exotoxin A from Pseudomonas aeruginosa. In some embodiments, the polypeptide is a variant of diphtheria toxoid that has been mutated to reduce or eliminate toxicity. In some embodiments, the polypeptide is $CRM_{197}$.

The polypeptide can be a polypeptide in which the toxin activity of the polypeptide can be at least partially mitigated. Examples of suitable polypeptides for use as in a saccharide-polypeptide conjugate are described, for example, in U.S. Pat. No. 8,808,707, which is incorporated herein in its entirety. Examples of polypeptides include, without limitation, polylysine, polyglutamic acid, polyaspartic acid, co-polymers thereof, and mixed polymers of these amino acids and others, e.g., serines, threonines, or tyrosines, to confer desirable solubility properties on the resultant loaded carrier and conjugate. Additionally, suitable polypeptide carriers may include bacterial toxins, toxoids, or inactivated toxins.

A toxoid can be a bacterial toxin whose toxicity has been weakened or suppressed while other properties, typically immunogenicity, are maintained.

As a class, bacterial toxins and derivatives thereof can to be highly immunogenic. Polypeptides derived from bacterial toxins may be effective at eliciting an immune response to saccharides of the conjugate. In some embodiments, the toxicity of the toxin (or derivative thereof) may be reduced. Steps may be taken (e.g., by chemical and/or genetic means) to render the toxins non-toxic and safe for administration to mammals. Examples of such bacterial toxin-derived polypeptides which may be used in the immunogenic saccharide carrier conjugates described herein include diphtheria and tetanus toxoids, and variants thereof (e.g., DT, $CRM_{197}$, tetanus toxoid (TT)), tetanus toxoid C peptide, cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B streptococcus, non-typable H. influenzae P4 protein, non-typable H. influenzae P6 protein, M catarrhalis uspA, keyhole limpet haemocyanin (KLH), bovine serum albumin (BSA), outer membrane protein complex C (OMPC), outer membrane protein complex C (OMPC) from N. meningitidis, porins, transferrin binding proteins, the purified protein derivative of tuberculin (PPD), E. coli LT, E. coli ST, exotoxin A from Pseudomonas aeruginosa, protein D from H. influenzae, or any fragment thereof. In some embodiments, the polypeptide is protein D from H. influenzae. In some embodiments, the polypeptide is an outer membrane complex C (OMPC). In some embodiments, the polypeptide is OMPC from N. meningitidis. In some embodiments, the polypeptide is tetanus toxoid.

In some embodiments, the carrier is a $CRM_{197}$. $CRM_{197}$ is a non-toxic variant (i.e., toxoid) of diphtheria toxin isolated from cultures of Corynebacterium diphtheria strain C7 (β197) grown in casamino acids and yeast extract-based medium. $CRM_{197}$ contains a point mutation at amino acid position 52 relative to the wild-type sequence, which substitutes a glycine residue with glutamic acid and eliminates enzymatic activity and toxicity. See, e.g., Giannini et al. Nucleic Acids Res. (1984) 12: 4063-9. In some embodiments, $CRM_{197}$ is purified through ultra-filtration, ammonium sulfate precipitation, and ion-exchange chromatography. Alternatively, CRM197 is prepared recombinantly as described in the art, e.g., U.S. Pat. No. 5,614,382, which is herein incorporated by reference.

Polypeptide fragments may be used to elicit a protective immune response against the capsular polysaccharide or fragment of the capsular polysaccharide of the immunogenic saccharide-polypeptide conjugate. These fragments may encompass T-helper epitopes.

The saccharides may be conjugated to the polypeptide by, e.g., chemical or biological synthesis. In some embodiments, the capsular polysaccharide or fragment of the capsular polysaccharide is conjugated to the polypeptide by chemical, enzymatic, or biological synthesis.

In some embodiments, a capsular polysaccharide or immunogenic fragment thereof is chemically activated and then reacted with a polypeptide. For example, capsular polysaccharides or fragments of the capsular polysaccharides can be conjugated to the polypeptide by reductive animation, reductive animation and attachment of a spacer linked to an active ester, carbodiimide-mediated coupling, cyanogen-bromide activation of polysaccharide or thioether bonding. In some embodiments, the immunogenic saccharide-polypeptide comprises the capsular polysaccharide at least partially embedded in the polypeptide. In some embodiments, the immunogenic saccharide-polypeptide comprises the capsular polysaccharide chemically cross-linked to the polypeptide. In some embodiments, the immunogenic saccharide-polypeptide comprises the capsular polysaccharide at least partially chemically cross-linked to the polypeptide.

In some embodiments, the capsular polysaccharide or fragment of the capsular polysaccharide of a serotype from *H. influenzae* can be conjugated to a polypeptide by chemical or biological synthesis. In some embodiments, one saccharide can be conjugated to one polypeptide. In some embodiments, two or more (e.g., 2, 3, 4, 5, or more) saccharides can be conjugated to one polypeptide. In some embodiments, two or more (e.g., 2, 3, 4, 5, or more) saccharides of the same serotype are conjugated to one polypeptide. In some embodiments, two or more (e.g., 2, 3, 4, 5, or more) saccharides of different serotypes are conjugated to one polypeptide. In some embodiments, one capsular polysaccharide or immunogenic fragment thereof is conjugated to one polypeptide. In some embodiments, two or more (e.g., 2, 3, 4, 5, or more) capsular polysaccharides or fragments thereof can be conjugated to one polypeptide. In some embodiments, two or more (e.g., 2, 3, 4, 5, or more) capsular polysaccharides or fragments thereof from the same serotype are conjugated to one polypeptide. In some embodiments, two or more (e.g., 2, 3, 4, 5, or more) capsular polysaccharides or fragments thereof different serotypes are conjugated to one polypeptide.

In some embodiments, the polypeptide is conjugated to an immunogenic serotype a capsular polysaccharide, or fragment thereof, isolated from *H. influenzae* serotype a. In some embodiments, the polypeptide is conjugated to an immunogenic serotype b capsular polysaccharide, or fragment thereof, isolated from *H. influenzae* serotype b. In some embodiments, the polypeptide is conjugated to an immunogenic serotype c capsular polysaccharide, or fragment thereof, isolated from *H. influenzae* serotype c. In some embodiments, the polypeptide is conjugated to an immunogenic serotype d capsular polysaccharide, or fragment thereof, isolated from *H. influenzae* serotype d. In some embodiments, the polypeptide is conjugated to an immunogenic serotype e capsular polysaccharide, or fragment thereof, isolated from *H. influenzae* serotype e. In some embodiments, the polypeptide is conjugated to an immunogenic serotype f capsular polysaccharide, or fragment thereof, isolated from *H. influenzae* serotype f.

In some embodiments, the carrier is $CRM_{197}$. In some embodiments, $CRM_{197}$ is conjugated to an immunogenic serotype a capsular polysaccharide or fragment thereof isolated from *H. influenzae* serotype a. In some embodiments, $CRM_{197}$ is conjugated to an immunogenic serotype b capsular polysaccharide or fragment thereof isolated from *H. influenzae* serotype b. In some embodiments, $CRM_{197}$ is conjugated to an immunogenic serotype c capsular polysaccharide or fragment thereof isolated from *H. influenzae* serotype c. In some embodiments, $CRM_{197}$ is conjugated to an immunogenic serotype d capsular polysaccharide or fragment thereof isolated from *H. influenzae* serotype d. In some embodiments, $CRM_{197}$ is conjugated to an immunogenic serotype e capsular polysaccharide or fragment thereof isolated from *H. influenzae* serotype e. In some embodiments, $CRM_{197}$ is conjugated to an immunogenic serotype f capsular polysaccharide or fragment thereof isolated from *H. influenzae* serotype f.

In some embodiments, the carrier is OMPC from *N. meningitidis*. In some embodiments, OMPC from *N. meningitidis* is conjugated to an immunogenic serotype a capsular polysaccharide or fragment thereof isolated from *H. influenzae* serotype a. In some embodiments, OMPC from *N. meningitidis* is conjugated to an immunogenic serotype b capsular polysaccharide or fragment thereof isolated from *H. influenzae* serotype b. In some embodiments, OMPC from *N. meningitidis* is conjugated to an immunogenic serotype c capsular polysaccharide or fragment thereof isolated from *H. influenzae* serotype c. In some embodiments, OMPC from *N. meningitidis* is conjugated to an immunogenic serotype d capsular polysaccharide or fragment thereof isolated from *H. influenzae* serotype d. In some embodiments, OMPC from *N. meningitidis* is conjugated to an immunogenic serotype e capsular polysaccharide or fragment thereof isolated from *H. influenzae* serotype e. In some embodiments, OMPC from *N. meningitidis* is conjugated to an immunogenic serotype f capsular polysaccharide or fragment thereof isolated from *H. influenzae* serotype f.

In some embodiments, the carrier is tetanus toxoid. In some embodiments, tetanus toxoid is conjugated to an immunogenic serotype a capsular polysaccharide or fragment thereof isolated from *H. influenzae* serotype a. In some embodiments, tetanus toxoid is conjugated to an immunogenic serotype b capsular polysaccharide or fragment thereof isolated from *H. influenzae* serotype b. In some embodiments, tetanus toxoid from *N. meningitidis* is conjugated to an immunogenic serotype c capsular polysaccharide or fragment thereof isolated from *H. influenzae* serotype c. In some embodiments, tetanus toxoid from *N. meningitidis* is conjugated to an immunogenic serotype d capsular polysaccharide or fragment thereof isolated from *H. influenzae* serotype d. In some embodiments, tetanus toxoid from *N. meningitidis* is conjugated to an immunogenic serotype e capsular polysaccharide or fragment thereof isolated from *H. influenzae* serotype e. In some embodiments, tetanus toxoid from *N. meningitidis* is conjugated to an immunogenic serotype f capsular polysaccharide or fragment thereof isolated from *H. influenzae* serotype f.

An immunogenic saccharide-polypeptide conjugate composition may have a molecular weight of about 50 kDa to about 12,500 kDa. In some embodiments, the immunogenic saccharide-polypeptide conjugate composition has a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa.

An immunogenic saccharide-polypeptide conjugate composition comprising a *H. influenzae* serotype a immunogenic saccharide may have a molecular weight of about 50 kDa to about 12,500 kDa. In some embodiments, the immunogenic saccharide-polypeptide conjugate composition comprising a *H. influenzae* serotype a immunogenic saccharide has a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa.

An immunogenic saccharide-polypeptide conjugate composition comprising a *H. influenzae* serotype b immunogenic saccharide may have a molecular weight of about 50 kDa to about 12,500 kDa. In some embodiments, the immunogenic saccharide-polypeptide conjugate composition comprising a *H. influenzae* serotype b immunogenic saccharide has a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa.

An immunogenic saccharide-polypeptide conjugate composition comprising a *H. influenzae* serotype c immunogenic saccharide may have a molecular weight of about 50 kDa to about 12,500 kDa. In some embodiments, the immunogenic saccharide-polypeptide conjugate composition comprising a *H. influenzae* serotype c immunogenic saccharide has a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa.

An immunogenic saccharide-polypeptide conjugate composition comprising *H. influenzae* serotype d immunogenic saccharide may have a molecular weight of about 50 kDa to 12,500 kDa. In some embodiments, the immunogenic saccharide-polypeptide conjugate composition comprising a *H. influenzae* serotype d immunogenic saccharide has a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa.

An immunogenic saccharide-polypeptide conjugate composition comprising a *H. influenzae* serotype e immunogenic saccharide may have a molecular weight of about 50 kDa to about 12,500 kDa. In some embodiments, the immunogenic saccharide-polypeptide conjugate composition comprising a *H. influenzae* serotype e immunogenic saccharide has a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa.

An immunogenic saccharide-polypeptide conjugate composition comprising a *H. influenzae* serotype f immunogenic saccharide may have a molecular weight of about 50 kDa to about 12,500 kDa. In some embodiments, the immunogenic saccharide-polypeptide conjugate composition comprising a *H. influenzae* serotype f immunogenic saccharide has a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa. An immunogenic saccharide-polypeptide conjugate composition may have a saccharide to polypeptide ratio (w/w) from 0.2 to 5. In some embodiments, the immunogenic saccharide-polypeptide conjugate composition has a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

An immunogenic saccharide-polypeptide conjugate composition comprising a *H. influenzae* serotype a immunogenic saccharide may have a saccharide to polypeptide ratio (w/w) from 0.2 to 5. In some embodiments, the immunogenic saccharide-polypeptide conjugate composition comprising a *H. influenzae* serotype a immunogenic saccharide has a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

An immunogenic saccharide-polypeptide conjugate composition comprising a *H. influenzae* serotype b immunogenic saccharide may have a saccharide to polypeptide ratio (w/w) from 0.2 to 5. In some embodiments, the immunogenic saccharide-polypeptide conjugate composition comprising a *H. influenzae* serotype b immunogenic saccharide has a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

An immunogenic saccharide-polypeptide conjugate composition comprising a *H. influenzae* serotype c immunogenic saccharide may have a saccharide to polypeptide ratio (w/w) from 0.2 to 5. In some embodiments, the immunogenic saccharide-polypeptide conjugate composition comprising a *H. influenzae* serotype c immunogenic saccharide has a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

An immunogenic saccharide-polypeptide conjugate composition comprising a *H. influenzae* serotype d immunogenic saccharide may have a saccharide to polypeptide ratio (w/w) from 0.2 to 5. In some embodiments, the immunogenic saccharide-polypeptide conjugate composition comprising a *H. influenzae* serotype d immunogenic saccharide has a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

An immunogenic saccharide-polypeptide conjugate composition comprising a *H. influenzae* serotype e immunogenic saccharide may have a saccharide to polypeptide ratio (w/w) from 0.2 to 5. In some embodiments, the immunogenic saccharide-polypeptide conjugate composition comprising a *H. influenzae* serotype e immunogenic saccharide has a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

An immunogenic saccharide-polypeptide conjugate composition comprising a *H. influenzae* serotype f immunogenic saccharide may have a saccharide to polypeptide ratio (w/w) from 0.2 to 5. In some embodiments, the immunogenic saccharide-polypeptide conjugate composition comprising a *H. influenzae* serotype f immunogenic saccharide has a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

An immunogenic saccharide-polypeptide conjugate composition may have a molecular weight of about 50 kDa to about 12,500 kDa and have a saccharide to polypeptide ratio (w/w) from about 0.2 to about 5.

Any of the immunogenic saccharide-polypeptide conjugate compositions described herein may comprise immunogenic saccharides from one or more *H. influenzae* serotype, wherein the immunogenic saccharides have a molecular weight of about 50 kDa to about 500 kDa, about 50 kDa to about 750 kDa, about 50 kDa to about 1,000 kDa, about 50 kDa to about 2,000 kDa, about 50 kDa to about 3,000 kDa, about 50 kDa to about 4,000 kDa, about 50 kDa to about 5,000 kDa, about 50 kDa to about 6,000 kDa, about 50 kDa to about 7,000 kDa, about 50 kDa to about 8,000 kDa, about 50 kDa to about 9,000 kDa, about 50 kDa to about 10,000 kDa, about 50 kDa to about 11,000 kDa, or about 50 kDa to about 12,000 kDa; and a saccharide to polypeptide ratio (w/w) from 0.2 to 1, 0.2 to 2, 0.2 to 3, 0.2 to 4, 0.5 to 1, 0.5 to 2, 0.5 to 3, 0.5 to 4, 0.5 to 5, 1 to 1.5, 1 to 2, 1 to 2.5, 1 to 3, 1 to 3.5, 1 to 4, 1 to 4.5, or 1 to 5.

In some embodiments, the immunogenic saccharide-polypeptide conjugate composition comprising a *H. influenzae* serotype a immunogenic saccharide has a molecular weight of 50 kDa to 12,500 kDa and has a saccharide to polypeptide ratio (w/w) from 0.2 to 5. In some embodiments, the immunogenic saccharide-polypeptide conjugate composition comprising a *H. influenzae* serotype b immunogenic saccharide has a molecular weight of 50 kDa to 12,500 kDa and has a saccharide to polypeptide ratio (w/w) from 0.2 to 5. In some embodiments, the immunogenic saccharide-polypeptide conjugate composition comprising a *H. influenzae* serotype c immunogenic saccharide has a molecular weight of 50 kDa to 12,500 kDa and has a saccharide to polypeptide ratio (w/w) from 0.2 to 5. In some embodiments, the immunogenic saccharide-polypeptide conjugate composition comprising a *H. influenzae* serotype d immunogenic saccharide has a molecular weight of from 50 kDa to 12,500 kDa and has a saccharide to polypeptide ratio (w/w) from 0.2 to 5. In some embodiments, the immunogenic saccharide-polypeptide conjugate composition comprising a *H. influenzae* serotype e immunogenic saccharide has a molecular weight of from 50 kDa to 12,500 kDa and has a saccharide to polypeptide ratio (w/w) from 0.2 to 5. In some embodiments, the immunogenic saccharide-polypeptide conjugate composition comprising a *H. influenzae* serotype f immunogenic saccharide has a molecular weight of from 50 kDa to 12,500 kDa and has a saccharide to polypeptide ratio (w/w) from 0.2 to 5.

In some embodiments, any of the saccharides as described herein may be conjugated to any of the polypeptides described herein. In some embodiments, any of the immunogenic saccharide-polypeptide conjugates described herein may be isolated and/or purified. In some embodiments, any of the immunogenic-polypeptide conjugates described herein may be subjected to one or more isolation and/or purification process.

In some embodiments, the carrier of an immunogenic saccharide-carrier conjugate is a lipid. In some embodiments, the lipid of an immunogenic saccharide-lipid conjugate is a glycosphingolipid. In some embodiments, the carrier of an immunogenic saccharide-carrier conjugate is a glycosphingolipid.

A lipid may be, in some embodiments, any lipid that allows for conjugation or coupling of saccharide and results in the display of the lipid or conjugate, or coupling in a way that induces a protective immune response against (directed toward) the saccharide. A glycosphingolipid may be, in some embodiments, any lipid that allows for conjugation or coupling of saccharide and results in the display of the glycosphingolipid or conjugate, or coupling in a way that induces a protective immune response against (directed toward) the saccharide.

A lipid may be, in some embodiments, any lipid that allows for conjugation or coupling of a capsular polysaccharide or fragment of the capsular polysaccharide and can result in the display of the lipid or conjugate, or coupling in a way that can induce a protective immune response against (directed toward) the capsular polysaccharide or fragment of the capsular polysaccharide. A glycosphingolipid can be any glycosphingolipid that allows for conjugation or coupling of a capsular polysaccharide or fragment of the capsular polysaccharide and can result in the display of the glycosphingolipid or conjugate, or coupling in a way that can induce a protective immune response against (directed toward) the capsular polysaccharide or fragment of the capsular polysaccharide.

In some embodiments, the lipid is a cerebroside comprising a ceramide with a galactose residue at the 1-hydroxyl group moiety or any related compound thereof. In some embodiments, the glycosphingolipid is a cerebroside comprising a ceramide with a galactose residue at the 1-hydroxyl group moiety or any related compound thereof. In some embodiments, the lipid is α-galactosylceramide or other agelasphin derivative, KRN7000 or structural analogs thereof, OCH (a sphingosine-truncated analog of α-galactosylceramide), C-glycoside of OCH, α-C-galactosylceramide, or isoglobotrihexosylceramide. In some embodiments, the glycosphingolipid is α-galactosylceramide or other agelasphin derivative, KRN7000 or structural analogs thereof, OCH (a sphingosine-truncated analog of α-galactosylceramide), C-glycoside of OCH, α-C-galactosylceramide, or isoglobotrihexosylceramide. Additionally, suitable lipid carriers or glycosphingolipid carriers can include any lipid or glycosphingolipid capable of activating iNKT cells or NK cells.

Examples of suitable glycosphingolipids and conjugation techniques for use as in a saccharide-glycosphingolipid conjugate are described, for example, in PCT Publication WO2013/178236, published Dec. 5, 2013, incorporated herein by reference. Additionally, examples of suitable lipids and conjugation techniques for use as in a saccharide-lipid conjugate are described, for example, in International PCT Publication, WO 2013/178236, published Dec. 5, 2013, which is incorporated herein by reference.

A saccharide may be conjugated to the glycosphingolipid by any method known in the art, e.g., chemical synthesis, enzymatic. A saccharide may be conjugated to the lipid by any method known in the art, e.g., chemical synthesis, enzymatic.

In some embodiments, *H. influenzae* capsular polysaccharide or a fragment of the capsular polysaccharide is covalently bound to the glycosphingolipid to produce the saccharide-glycosphingolipid conjugate. In some embodiments, the *H. influenzae* capsular polysaccharide or a fragment of the capsular polysaccharide is covalently bound to an oxygen atom of the glycosphingolipid to produce the saccharide-glycosphingolipid conjugate. In some embodiments, *H. influenzae* capsular polysaccharide or a fragment of the capsular polysaccharide is covalently bound to a glycosphingolipid to produce the saccharide-glycosphingolipid conjugate. A capsular polysaccharide or fragment of the capsular polysaccharide can be covalently bound to an oxygen atom of a glycosphingolipid to produce the saccharide-glycosphingolipid conjugate. In some embodiments, the *H. influenzae* capsular polysaccharide or a fragment of the capsular polysaccharide is covalently bound to a hydroxyl group of a glycosphingolipid to produce the saccharide-glycosphingolipid conjugate. In some embodiments, the *H. influenzae* capsular polysaccharide or a fragment of the capsular polysaccharide is covalently bound to a sugar moiety of a glycosphingolipid to produce the saccharide-glycosphingolipid conjugate. In some embodiments, the *H. influenzae* capsular polysaccharide or a fragment of the capsular polysaccharide is covalently bound to an oxygen atom of a sugar moiety of a glycosphingolipid to produce the saccharide-glycosphingolipid conjugate. In some embodiments, the *H. influenzae* capsular polysaccharide or a fragment of the capsular polysaccharide is covalently bound to a hydroxyl group of a sugar moiety of a glycosphingolipid to produce the saccharide-glycosphingolipid conjugate.

In some embodiments, the glycosphingolipid is a α-galactosylceramide. In some embodiments, the *H. influenzae* capsular polysaccharide or a fragment of the capsular polysaccharide is covalently bound to α-galactosylceramide to produce the saccharide-glycosphingolipid conjugate. In some embodiments, the *H. influenzae* capsular polysaccharide or a fragment of the capsular polysaccharide is covalently bound to an oxygen of α-galactosylceramide to produce the saccharide-glycosphingolipid conjugate. In some embodiments, the *H. influenzae* capsular polysaccharide or a fragment of the capsular polysaccharide is covalently bound to a hydroxyl group of α-galactosylceramide to produce the saccharide-glycosphingolipid conjugate. In some embodiments, the *H. influenzae* capsular polysaccharide or a fragment of the capsular polysaccharide is covalently bound to a sugar moiety of α-galactosylceramide to produce the saccharide-glycosphingolipid conjugate. In some embodiments, the *H. influenzae* capsular polysaccharide or fragment of the capsular polysaccharide is covalently bound to an oxygen atom of a sugar moiety of α-galactosylceramide to produce the saccharide-glycosphingolipid conjugate. In some embodiments, the *H. influenzae* capsular polysaccharide or a fragment of the capsular polysaccharide is covalently bound to a hydroxyl group of a sugar moiety of α-galactosylceramide to produce the saccharide-glycosphingolipid conjugate.

In some embodiments, the *H. influenzae* capsular polysaccharide or a fragment of the capsular polysaccharide is covalently bound to the lipid to produce the saccharide-lipid conjugate. In some embodiments, the *H. influenzae* capsular polysaccharide or a fragment of the capsular polysaccharide is covalently bound to the lipid to produce the saccharide-lipid conjugate. In some embodiments, the *H. influenzae* capsular polysaccharide or a fragment of the capsular polysaccharide is covalently bound to an oxygen atom of the lipid to produce the saccharide-lipid conjugate. In some embodiments, the *H. influenzae* capsular polysaccharide or a fragment of the capsular polysaccharide is covalently bound to a lipid to produce the saccharide-lipid conjugate. In some embodiments, the *H. influenzae* capsular polysaccharide or a fragment of the capsular polysaccharide is covalently bound to an oxygen atom of a lipid to produce the saccharide-lipid conjugate. In some embodiments, the *H. influenzae* capsular polysaccharide or a fragment of the capsular polysaccharide is covalently bound to a hydroxyl group of a lipid to produce the saccharide-lipid conjugate.

In some embodiments, the lipid is a glycosphingolipid or α-galactosylceramide. In some embodiments, the *H. influenzae* capsular polysaccharide or a fragment of the capsular polysaccharide is covalently bound to a sugar moiety of a lipid to produce the saccharide-lipid conjugate. In some embodiments, the capsular polysaccharide or a fragment of the capsular polysaccharide is covalently bound to an oxygen atom of a sugar moiety of a lipid to produce the saccharide-lipid conjugate. In some embodiments, the *H. influenzae* capsular polysaccharide or a fragment of the capsular polysaccharide is covalently bound to a hydroxyl group of a sugar moiety of a lipid to produce the saccharide-lipid conjugate.

Additionally or alternatively, the *H. influenzae* capsular polysaccharide, or immunogenic fragment thereof, can be chemically activated and then reacted with the glycosphingolipid or lipid. In some embodiments, the glycosphingolipid or lipid is a glycosphingolipid or lipid linked to a linker, which can then be reacted with the capsular polysaccharide or immunogenic fragment thereof. In some embodiments, the glycosphingolipid or lipid is conjugated to the polysaccharide via a linker. In some embodiments, the glycosphingolipid or lipid is α-galactosylceramide. In some embodiments, the lipid is a glycosphingolipid. In some embodiments, the capsular polysaccharide or fragment of the capsular polysaccharide of a serotype from *H. influenzae* is directly conjugated to a glycosphingolipid or lipid by chemical synthesis or covalently conjugated to a linker linked to a glycosphingolipid or lipid. In some embodiments, one saccharide is conjugated to one glycosphingolipid. In some embodiments, one saccharide is conjugated to one lipid. In some embodiments, two or more glycosphingolipids is conjugated to one saccharide. In some embodiments, two or more lipids are conjugated to one saccharide. In some embodiments, two or more saccharides are conjugated to one glycosphingolipid. In some embodiments, two or more saccharides are conjugated to one lipid. In some embodiments, the saccharides are from the same serotype of *H. influenzae*. In some embodiments, the saccharides are from different serotypes of *H. influenzae*.

In some embodiments, the carrier of the immunogenic saccharide-carrier conjugate is a glycosphingolipid. In some embodiments, a glycosphingolipid is conjugated to an immunogenic serotype a capsular polysaccharide or fragment thereof isolated from *H. influenzae* serotype a. In some embodiments, a glycosphingolipid is conjugated to an immunogenic serotype b capsular polysaccharide or fragment thereof isolated from *H. influenzae* serotype b. In some embodiments, a glycosphingolipid is conjugated to an immunogenic serotype c capsular polysaccharide or fragment thereof isolated from *H. influenzae* serotype c. In some embodiments, a glycosphingolipid is conjugated to an immunogenic serotype d capsular polysaccharide or fragment thereof isolated from *H. influenzae* serotype d. In some embodiments, a glycosphingolipid is conjugated to an immunogenic serotype e capsular polysaccharide or fragment thereof isolated from *H. influenzae* serotype e. In some embodiments, a glycosphingolipid is conjugated to an immunogenic serotype f capsular polysaccharide or fragment thereof isolated from *H. influenzae* serotype f.

In some embodiments, the glycosphingolipid is α-galactosylceramide. In some embodiments, the glycosphingolipid is directly conjugated to the capsular polysaccharide isolated from a specific serotype or fragment thereof. Alternatively, in some embodiments, the glycosphingolipid can be conjugated via linker. The linker or direct conjugation of the capsular polysaccharide serotype or fragment thereof can be conjugated, for example, via an oxygen atom or via a hydroxyl group of the glycosphingolipid. In some embodiments, the linker or direct conjugation of the capsular polysaccharide or fragment thereof is conjugated via an oxygen atom of the sugar moiety of the glycosphingolipid. In some embodiments, the linker or direct conjugation of the capsular polysaccharide, or fragment thereof, is conjugated via a hydroxyl group of the sugar moiety of the glycosphingolipid.

In some embodiments, the carrier of the immunogenic saccharide-carrier conjugate is a lipid. In some embodiments, a lipid is conjugated to an immunogenic serotype a capsular polysaccharide or fragment thereof isolated from *H. influenzae* serotype a. In some embodiments, a lipid is conjugated to an immunogenic serotype b capsular polysaccharide or fragment thereof isolated from *H. influenzae* serotype b. In some embodiments, a lipid is conjugated to an immunogenic serotype c capsular polysaccharide or fragment thereof isolated from *H. influenzae* serotype c. In some embodiments, a lipid is conjugated to an immunogenic serotype d capsular polysaccharide or fragment thereof isolated from *H. influenzae* serotype d. In some embodiments, the lipid is conjugated to an immunogenic serotype e capsular polysaccharide or fragment thereof isolated from *H. influenzae* serotype e. In some embodiments, the lipid is conjugated to an immunogenic serotype f capsular polysaccharide or fragment thereof isolated from *H. influenzae* serotype f.

In some embodiments, the lipid is a glycosphingolipid. In some embodiments, the lipid is α-galactosylceramide. In some embodiment, the lipid can be directly conjugated to the capsular polysaccharide serotype or fragment thereof. Alternatively, in some embodiments, the lipid can be conjugated via linker. The linker or direct conjugation of the capsular polysaccharide serotype or fragment thereof can be conjugated via an oxygen atom or via a hydroxyl group of the lipid. In some embodiments, the linker or direct conjugation of the capsular polysaccharide or fragment thereof can be conjugated via an oxygen atom of the sugar moiety of the lipid. In some embodiments, the linker or direct conjugation of the capsular polysaccharide serotype or fragment thereof can be conjugated via a hydroxyl group of the lipid. In some embodiments, the linker or direct conjugation of the capsular polysaccharide or fragment thereof can be conjugated via a hydroxyl group of the sugar moiety of the lipid.

In some embodiments, α-galactosylceramide is conjugated to an immunogenic serotype a capsular polysaccharide or fragment thereof isolated from *H. influenza* serotype a. In some embodiments, α-galactosylceramide is conjugated to an immunogenic serotype b capsular polysaccharide or fragment thereof isolated from *H. influenzae* serotype b. In some embodiments, α-galactosylceramide is conjugated to an immunogenic serotype c capsular polysaccharide or fragment thereof isolated from *H. influenzae* serotype c. In some embodiments, α-galactosylceramide is conjugated to an immunogenic serotype d capsular polysaccharide or fragment thereof isolated from *H. influenzae* serotype d. In some embodiments, α-galactosylceramide is conjugated to an immunogenic serotype e capsular polysaccharide or fragment thereof isolated from *H. influenzae* serotype e. In some embodiments, α-galactosylceramide is conjugated to an immunogenic serotype f capsular polysaccharide or fragment thereof isolated from *H. influenzae* serotype f.

In some embodiments, the immunogenic saccharide-glycosphingolipid conjugate composition has a molecular weight of from about 25 kDa to about 12,500 kDa. In some embodiments, the immunogenic saccharide-glycosphingolipid conjugate composition has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

In some embodiments, the immunogenic saccharide-glycosphingolipid conjugate composition comprising a *H. influenzae* serotype a immunogenic saccharide has a molecular weight of from about 25 kDa to about 12,500 kDa. In some embodiments, the immunogenic saccharide-glycosphingolipid conjugate composition comprising a *H. influenzae* serotype a immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

In some embodiments, the immunogenic saccharide-glycosphingolipid conjugate composition comprising a *H. influenzae* serotype b immunogenic saccharide has a molecular weight of from 25 kDa to 12,500 kDa. In some embodiments, the immunogenic saccharide-glycosphingolipid conjugate composition comprising a *H. influenzae* serotype b immunogenic saccharide has a molecular weight of about 25 kDa to about 500 kDa, about 25 kDa to about 750 lcDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

In some embodiments, the immunogenic saccharide-glycosphingolipid conjugate composition comprising a *H. influenzae* serotype c immunogenic saccharide has a molecular weight of from 25 kDa to 12,500 kDa. In some embodiments, the immunogenic saccharide-glycosphingolipid conjugate composition comprising a *H. influenzae* serotype c immunogenic saccharide can have a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

In some embodiments, the immunogenic saccharide-glycosphingolipid conjugate composition comprising a *H. influenzae* serotype d immunogenic saccharide has a molecular weight of from 25 kDa to 12,500 kDa. In some embodiments, the immunogenic saccharide-glycosphingolipid conjugate composition comprising a *H. influenzae* serotype d immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

In some embodiments, the immunogenic saccharide-glycosphingolipid conjugate composition comprising a *H. influenzae* serotype e immunogenic saccharide has a molecular weight of from 25 kDa to 12,500 kDa. In some embodiments, the immunogenic saccharide-glycosphingolipid conjugate composition comprising a *H. influenzae* serotype e immunogenic saccharide can have a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

In some embodiments, the immunogenic saccharide-glycosphingolipid conjugate composition comprising a *H. influenzae* serotype f immunogenic saccharide has a molecular weight of from 25 kDa to 12,500 kDa. In some embodiments, the immunogenic saccharide-glycosphingolipid conjugate composition comprising a *H. influenzae* serotype f immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

In some embodiments, the immunogenic saccharide-glycosphingolipid conjugate composition has a saccharide to glycosphingolipid ratio (w/w) from about 5 to about 24,000. In some embodiments, the immunogenic saccharide-glycosphingolipid conjugate composition has a saccharide to glycosphingolipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-glycosphingolipid conjugate composition comprising a *H. influenzae* serotype a immunogenic saccharide has a saccharide to glycosphingolipid ratio (w/w) from 5 to 24,000. In some embodiments, the immunogenic saccharide-glycosphingolipid conjugate composition comprising a *H. influenzae* serotype a immunogenic saccharide has a saccharide to glycosphingolipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-glycosphingolipid conjugate composition comprising a *H. influenzae* serotype b immunogenic saccharide has a saccharide to glycosphingolipid ratio (w/w) from 5 to 24,000. In some embodiments, the immunogenic saccharide-glycosphingolipid conjugate composition comprising a *H. influenzae* serotype b immunogenic saccharide has a saccharide to glycosphingolipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-glycosphingolipid conjugate composition comprising a *H. influenzae* serotype c immunogenic saccharide has a saccharide to glycosphingolipid ratio (w/w) from 5 to 24,000. In some embodiments, the immunogenic saccharide-glycosphingolipid conjugate composition comprising a *H. influenzae* serotype c immunogenic saccharide has a saccharide to glycosphingolipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-glycosphingolipid conjugate composition comprising a *H. influenzae* serotype d immunogenic saccharide has a saccharide to glycosphingolipid ratio (w/w) from 5 to 24,000. In some embodiments, the immunogenic saccharide-glycosphingolipid conjugate composition comprising a *H. influenzae* serotype d immunogenic saccharide has a saccharide to glycosphingolipid ratio (w/w) about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-glycosphingolipid conjugate composition comprising a *H. influenzae* serotype e immunogenic saccharide has a saccharide to glycosphingolipid ratio (w/w) from 5 to 24,000. In some embodiments, the immunogenic saccharide-glycosphingolipid conjugate composition comprising a *H. influenzae* serotype e immunogenic saccharide has a saccharide to glycosphingolipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-glycosphingolipid conjugate composition comprising a *H.*

*influenzae* serotype f immunogenic saccharide has a saccharide to glycosphingolipid ratio (w/w) from 5 to 24,000. In some embodiments, the immunogenic saccharide-glycosphingolipid conjugate composition comprising a *H. influenzae* serotype f immunogenic saccharide has a saccharide to glycosphingolipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-glycosphingolipid conjugate composition may have a molecular weight of from about 50 kDa to about 12,500 kDa and a saccharide to glycosphingolipid ratio (w/w) from 5 to 24,000.

Any of the immunogenic saccharide-glycosphingolipid conjugate compositions described herein may comprise immunogenic saccharides from one or more *H. influenzae* serotype, wherein the immunogenic saccharides have a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa; and a saccharide to glycosphingolipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-glycosphingolipid conjugate composition comprising a *H. influenzae* serotype a immunogenic saccharide has a molecular weight of from 25 kDa to 12,500 kDa and has a saccharide to glycosphingolipid ratio (w/w) from 5 to 24,000. In some embodiments, the immunogenic saccharide-glycosphingolipid conjugate composition comprising a *H. influenzae* serotype b immunogenic saccharide has a molecular weight of from 25 kDa to 12,500 kDa and has a saccharide to glycosphingolipid ratio (w/w) from 5 to 24,000. In some embodiments, the immunogenic saccharide-glycosphingolipid conjugate composition comprising a *H. influenzae* serotype c immunogenic saccharide has a molecular weight of from 25 kDa to 12,500 kDa and has a saccharide to glycosphingolipid ratio (w/w) from 5 to 24,000. In some embodiments, the immunogenic saccharide-glycosphingolipid conjugate composition comprising a *H. influenzae* serotype d immunogenic saccharide has a molecular weight of from 25 kDa to 12,500 kDa and has a saccharide to glycosphingolipid ratio (w/w) from 5 to 24,000. In some embodiments, the immunogenic saccharide-glycosphingolipid conjugate composition comprising a *H. influenzae* serotype e immunogenic saccharide has a molecular weight of from 25 kDa to 12,500 kDa and has a saccharide to glycosphingolipid ratio (w/w) from 5 to 24,000. In some embodiments, the immunogenic saccharide-glycosphingolipid conjugate composition comprising a *H. influenzae* serotype f immunogenic saccharide has a molecular weight of from 25 kDa to 12,500 kDa and has a saccharide to glycosphingolipid ratio (w/w) from 5 to 24,000.

An immunogenic saccharide-lipid conjugate composition may have a molecular weight of about 25 kDa to about 12,500 kDa. In some embodiments, the immunogenic saccharide-lipid conjugate composition has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

An immunogenic saccharide-lipid conjugate composition comprising *H. influenzae* serotype a immunogenic saccharide may have a molecular weight of about 25 kDa to about 12,500 kDa. In some embodiments, the immunogenic saccharide-polypeptide conjugate composition comprising a *H. influenzae* serotype a immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

An immunogenic saccharide-lipid conjugate composition comprising *H. influenzae* serotype b immunogenic saccharide may have a molecular weight of 25 kDa to 12,500 kDa. In some embodiments, the immunogenic saccharide-lipid conjugate composition comprising a *H. influenzae* serotype b immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

An immunogenic saccharide-lipid conjugate composition comprising a *H. influenzae* serotype c immunogenic saccharide may have a molecular weight of 25 kDa to 12,500 kDa. In some embodiments, the immunogenic saccharide-lipid conjugate composition comprising *H. influenzae* serotype c immunogenic saccharide has a molecular weight of about 25 kDa to about 500 kDa, about 25 kDa to about 750 lcDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

An immunogenic saccharide-lipid conjugate composition comprising a *H. influenzae* serotype d immunogenic saccharide may have a molecular weight of about 25 kDa to about 12,500 kDa. In some embodiments, the immunogenic saccharide-lipid conjugate composition comprising a *H. influenzae* serotype d immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

An immunogenic saccharide-lipid conjugate composition comprising *H. influenzae* serotype e immunogenic saccharide may have a molecular weight of about 25 kDa to about 12,500 kDa. In some embodiments, the immunogenic saccharide-lipid conjugate composition comprising a *H. influenzae* serotype e immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

An immunogenic saccharide-lipid conjugate composition comprising a *H. influenzae* serotype f immunogenic saccharide may have a molecular weight of from about 25 kDa to about 12,500 kDa. In some embodiments, the immunogenic saccharide-lipid conjugate composition comprising a *H. influenzae* serotype f immunogenic saccharide has a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa.

An immunogenic saccharide-lipid conjugate composition may have a saccharide to lipid ratio (w/w) from about 5 to about 24,000. In some embodiments, the immunogenic saccharide-lipid conjugate composition has a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-lipid conjugate composition comprising a *H. influenzae* serotype a immunogenic saccharide may have a saccharide to lipid ratio (w/w) from 5 to 24,000. In some embodiments, the immunogenic saccharide-lipid conjugate composition comprising a *H. influenzae* serotype a immunogenic saccharide has a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-lipid conjugate composition comprising a *H. influenzae* serotype b immunogenic saccharide may have a saccharide to lipid ratio(w/w) from 5 to 24,000. In some embodiments, the immunogenic saccharide-lipid conjugate composition comprising a *H. influenzae* serotype b immunogenic saccharide has a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-lipid conjugate composition comprising a *H. influenzae* serotype c immunogenic saccharide may have a saccharide to lipid ratio(w/w) from 5 to 24,000. In some embodiments, the immunogenic saccharide-lipid conjugate composition comprising a *H. influenzae* serotype c immunogenic saccharide has a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-lipid conjugate composition comprising a *H. influenzae* serotype d immunogenic saccharide may have a saccharide to lipid ratio(w/w) from 5 to 24,000. In some embodiments, the immunogenic saccharide-lipid conjugate composition comprising a *H. influenzae* serotype d immunogenic saccharide has a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-lipid conjugate composition comprising a *H. influenzae* serotype e immunogenic saccharide may have a saccharide to lipid ratio (w/w) from 5 to 24,000. In some embodiments, the immunogenic saccharide-lipid conjugate composition comprising a *H. influenzae* serotype e immunogenic saccharide has a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-lipid conjugate composition comprising a *H. influenzae* serotype f immunogenic saccharide may have a saccharide to lipid ratio (w/w) from 5 to 24,000. In some embodiments, the immunogenic saccharide-lipid conjugate composition comprising a *H. influenzae* serotype f immunogenic saccharide has a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

An immunogenic saccharide-lipid conjugate composition may have a molecular weight of from 50 kDa to 12,500 kDa and have a saccharide to lipid ratio (w/w) from 5 to 24,000.

Any of the immunogenic saccharide-lipid conjugate compositions described herein may comprise immunogenic saccharides from one or more *H. influenzae* serotype, wherein the immunogenic saccharides have a molecular weight of about 25 kDa to about 500 kDa, about 25 kDa to about 750 kDa, about 25 kDa to about 1,000 kDa, about 25 kDa to about 2,000 kDa, about 25 kDa to about 3,000 kDa, about 25 kDa to about 4,000 kDa, about 25 kDa to about 5,000 kDa, about 25 kDa to about 6,000 kDa, about 25 kDa to about 7,000 kDa, about 25 kDa to about 8,000 kDa, about 25 kDa to about 9,000 kDa, about 25 kDa to about 10,000 kDa, about 25 kDa to about 11,000 kDa, or about 25 kDa to about 12,000 kDa; and a saccharide to lipid ratio (w/w) from about 5 to about 100, about 5 to about 500, about 5 to about 1,000, about 5 to about 5,000, about 5 to about 10,000, about 5 to about 15,000, about 5 to about 20,000, about 83 to about 1,000, about 83 to about 5,000, about 83 to about 10,000, about 83 to about 15,000, about 83 to about 20,000, or about 83 to about 24,000.

In some embodiments, the immunogenic saccharide-lipid conjugate composition comprising a *H. influenzae* serotype a immunogenic saccharide has a molecular weight of 25 kDa to 12,500 kDa and has a saccharide to lipid ratio (w/w) from 5 to 24,000. In some embodiments, the immunogenic saccharide-lipid conjugate composition comprising a *H. influenzae* serotype b immunogenic saccharide has a molecular weight of 25 kDa to 12,500 kDa and has a saccharide to lipid ratio (w/w) from 5 to 24,000. In some embodiments, the immunogenic saccharide-lipid conjugate composition comprising a *H. influenzae* serotype c immunogenic saccharide has a molecular weight of 25 kDa to 12,500 kDa and has a saccharide to lipid ratio (w/w) from 5 to 24,000. In some embodiments, the immunogenic saccharide-lipid conjugate composition comprising a *H. influenzae* serotype d immunogenic saccharide has a molecular weight of 25 kDa to 12,500 kDa and has a saccharide to lipid ratio (w/w) from 5 to 24,000. In some embodiments, the immunogenic saccharide-lipid conjugate composition comprising a *H. influenzae* serotype e immunogenic saccharide has a molecular weight of 25 kDa to 12,500 kDa and has a saccharide to lipid ratio (w/w) from 5 to 24,000. In some embodiments, the immunogenic saccharide-lipid conjugate composition comprising a *H. influenzae* serotype f immunogenic saccharide has a molecular weight of 25 kDa to 12,500 kDa and has a saccharide to lipid ratio (w/w) from 5 to 24,000.

In some embodiments, any of the saccharides as described herein may be conjugated to any of the glycosphingolipids described herein. In some embodiments, any of the saccharides as described herein may be conjugated to any of the lipids described herein. Any of the immunogenic saccharide-lipid conjugates described herein may be isolated and/or purified. In some embodiments, any of the immunogenic saccharide-lipid conjugates described herein may be subjected to one or more isolation and/or purification processes.

Pharmaceutical Compositions

Also within the scope of the present disclosure are pharmaceutical compositions comprising immunogenic saccharide-carrier conjugates. As used herein, a pharmaceutical composition is a composition that is for administration to a subject. In some embodiments, the pharmaceutical composition comprises any one or more of the saccharide-carrier conjugates described herein. In some embodiments, the pharmaceutical compositions are for prophylactic administration to a subject (e.g., a subject at risk of infection with *H. influenzae*). In some embodiments, administration of the pharmaceutical compositions reduces or prevents infection with *H. influenzae* (e.g., the incidence of infection) and/or reduces the severity of infection with *H. influenzae* (e.g., one or more symptoms, duration).

In some embodiments, the saccharide-polypeptide conjugates described herein are in the form of a pharmaceutical composition. In some embodiments, the saccharide-glycosphingolipid conjugates described herein are in the form of a pharmaceutical composition. In some embodiments, the saccharide-lipid conjugates described herein are in the form of a pharmaceutical composition.

In some embodiments, the saccharide-polypeptide conjugates described herein are in the form of a pharmaceutical composition in unit dose form. In some embodiments, the saccharide-glycosphingolipid conjugates described herein are in the form of a pharmaceutical composition in unit dose form. In some embodiments, the saccharide-lipid conjugates described herein are in the form of a pharmaceutical composition in unit dose form.

Optimum doses of an immunogenic saccharide-carrier conjugate can be assessed by one of skill in the art, such as a medical practitioner. A dose may be measured as the amount of the saccharide-carrier conjugate administered to the subject or the amount of the saccharide administered (in the form of the saccharide-carrier conjugate). In some embodiments, a dose of saccharide-carrier conjugate comprises between 0.1 and 100 µg of the saccharide per dose. In some embodiments, saccharide-carrier conjugate comprises between 5 and 20 µg per saccharide per dose.

In general, a pharmaceutical composition that is administered to a subject prophylactically (e.g., prior to infection with *H. influenzae* or a specific serotype thereof) may be referred to as a vaccine. In some embodiments, the saccharide-polypeptide conjugates described herein are in the form of a vaccine. In some embodiments, the saccharide-glycosphingolipid conjugates described herein are in the form of a vaccine. In some embodiments, the saccharide-lipid conjugates described herein are in the form of a vaccine. Any of the pharmaceutical compositions and/or vaccines described herein may comprise an adjuvant.

In some embodiments, the pharmaceutical composition comprises an immunogenic saccharide-polypeptide conjugate. In some embodiments, the pharmaceutical composition comprises an immunogenic saccharide-glycosphingolipid conjugate. In some embodiments, the pharmaceutical composition comprises an immunogenic saccharide-lipid conjugate. In some embodiments, the pharmaceutical composition comprises an immunogenic capsular polysaccharide-polypeptide conjugate.

In some embodiments, the pharmaceutical composition comprises an immunogenic capsular polysaccharide-glycosphingolipid conjugate. In some embodiments, the pharmaceutical composition comprises an immunogenic capsular polysaccharide-lipid conjugate. In some embodiments, the pharmaceutical composition is in unit dose form and comprises an immunogenic capsular polysaccharide-polypeptide conjugate. In some embodiments, the pharmaceutical composition is in unit dose form and comprises an immunogenic capsular polysaccharide-polypeptide conjugate. In some embodiments, the pharmaceutical composition is in unit dose form and comprises an immunogenic capsular polysaccharide-polypeptide conjugate. In some embodiments, the pharmaceutical composition comprises an immunogenic saccharide-polypeptide conjugate, wherein the capsular polysaccharide, or immunogenic fragment thereof, of the saccharide-polypeptide conjugate is from one serotype of *H. influenzae*. In some embodiments, the pharmaceutical composition comprises an immunogenic saccharide-glycosphingolipid conjugate wherein the capsular polysaccharide, or immunogenic fragment thereof, of the saccharide-glycosphingolipid conjugate is from one serotype of *H. influenzae*. In some embodiments, the pharmaceutical composition comprises an immunogenic saccharide-lipid conjugate wherein the capsular polysaccharide, or immunogenic fragment thereof, of the saccharide-lipid conjugate can be from one serotype of *H. influenzae*.

Also within the scope of the present disclosure are pharmaceutical compositions comprising immunogenic saccharide-carrier conjugates, wherein the capsular polysaccharides are from more than one (e.g., 2, 3, 3, 4, 5, or more) serotypes of *H. influenzae*. In some embodiments, the pharmaceutical composition comprises an immunogenic saccharide-polypeptide conjugates wherein the capsular polysaccharides, or immunogenic fragments thereof, can be from different serotypes, creating a mixture of different immunogenic saccharide-polypeptide conjugates. In some embodiments, the pharmaceutical composition comprises immunogenic saccharide-glycosphingolipid conjugates, wherein the capsular polysaccharides, or immunogenic fragments thereof, can be from different serotypes, creating a mixture of different immunogenic saccharide-glycosphingolipid conjugates. In some embodiments, the pharmaceutical composition comprises immunogenic saccharide-lipid conjugates wherein the capsular polysaccharides, or immunogenic fragments thereof, can be from different serotypes, creating a mixture of different immunogenic saccharide-lipid conjugates.

In some embodiments, the pharmaceutical composition comprises a saccharide-polypeptide conjugate comprising a capsular polysaccharide or immunogenic fragment thereof from a serotype of $H.$ $influenzae$ conjugated to a polypeptide, and wherein the serotype is at least one of a, c, d, e, or f; or a combination thereof. In some embodiments, the pharmaceutical composition comprises a plurality of saccharide-polypeptide conjugates comprising at least 2, 3, 4, 5, 6, 7, 8, or 9 serotypes selected from the group consisting of a, b, c, d, e, and f. In some embodiments, the pharmaceutical composition comprises a plurality of saccharide-polypeptide conjugates comprising saccharides from $H.$ $influenzae$ serotype a and at least one additional serotype, such as serotype b, c, d, e, or f. In some embodiments, the pharmaceutical composition comprises a plurality of saccharide-polypeptide conjugates comprising saccharides from $H.$ $influenzae$ serotype b and at least one additional serotype, such as a, c, d, e, or f. In some embodiments, the pharmaceutical composition comprises a plurality of saccharide-polypeptide conjugates comprising saccharides from $H.$ $influenzae$ serotype c and at least one additional serotype, such as b, a, d, e, or f. In some embodiments, the pharmaceutical composition comprises a plurality of saccharide-polypeptide conjugates comprising saccharides from $H.$ $influenzae$ serotype d and at least one additional serotype, such as b, c, a, e, or f. In some embodiments, the pharmaceutical composition comprises a plurality of saccharide-polypeptide conjugates comprising saccharides from $H.$ $influenzae$ serotype e and at least one additional serotype, such as b, c, d, a, or f. In some embodiments, the pharmaceutical composition comprises a plurality of saccharide-polypeptide conjugates comprising saccharides from $H.$ $influenzae$ serotype f and at least one additional serotype comprising a, b, c, d, or e.

In some embodiments, the pharmaceutical composition comprises a plurality of saccharide-polypeptide conjugates comprising saccharides from $H.$ $influenzae$ serotype a and serotype b. In some embodiments, the pharmaceutical composition comprises a plurality of saccharide-polypeptide conjugates comprising saccharides from $H.$ $influenzae$ serotype a and serotype c. In some embodiments, the pharmaceutical composition comprises a plurality of saccharide-polypeptide conjugates comprising saccharides from $H.$ $influenzae$ serotype a and serotype d. In some embodiments, the pharmaceutical composition comprises a plurality of saccharide-polypeptide conjugates comprising saccharides from $H.$ $influenzae$ serotype a and serotype e. In some embodiments, the pharmaceutical composition comprises a plurality of saccharide-polypeptide conjugates comprising saccharides from $H.$ $influenzae$ serotype a and serotype f. In some embodiments, the pharmaceutical composition comprises a plurality of saccharide-polypeptide conjugates comprising saccharides from $H.$ $influenzae$ serotype a and any combination of saccharides from $H.$ $influenzae$ serotypes serotype b, c, d, e, and/or f.

The immunogenic saccharide-polypeptide conjugate(s) can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition. In some embodiments, the pharmaceutical composition comprises a plurality of saccharide-carrier conjugates, wherein each of the saccharide carrier conjugates is present in the composition in equal amounts. In some embodiments, the pharmaceutical composition comprises a plurality of saccharide-carrier conjugates, wherein one or more of the saccharide carrier conjugates is present in the composition in a different amount. In some embodiments, each of the saccharide-carrier conjugate is present in the composition at an amount between about 0.001, 0.01, 0.1, 1, 2, 3, 4, 5, 6, 7, 8, 9, 10, 20, 30, 40, 50, 60, 70, 80, 90, 95, or 100%, by weight.

Any of the pharmaceutical compositions comprising immunogenic saccharide-polypeptide conjugate(s) described herein can include excipients that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition. Any of the pharmaceutical compositions comprising the immunogenic saccharide-polypeptide conjugate(s) described herein can include adjuvants that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition.

In some embodiments, the pharmaceutical composition comprises a saccharide-glycosphingolipid conjugate comprising a capsular polysaccharide or immunogenic fragment thereof from a serotype of $H.$ $influenzae$ conjugated to a glycosphingolipid, and wherein the serotype is at least one of a, c, d, e, or f; or a combination thereof. In some embodiments, the pharmaceutical composition comprises a plurality of saccharide-glycosphingolipid conjugates comprising at least 2, 3, 4, 5, 6, 7, 8, or 9 serotypes selected from the group consisting of a, b, c, d, e, and f. In some embodiments, the pharmaceutical composition comprises a plurality of saccharide-glycosphingolipid conjugates comprising saccharides from $H.$ $influenzae$ serotype a and at least one additional serotype, such as b, c, d, e, or f. In some embodiments, the pharmaceutical composition comprises a plurality of saccharide-glycosphingolipid conjugates comprising saccharides from $H.$ $influenzae$ serotype b and at least one additional serotype, such as a, c, d, e, or f. In some embodiments, the pharmaceutical composition comprises a plurality of saccharide-glycosphingolipid conjugates comprising saccharides from $H.$ $influenzae$ serotype c and at least one additional serotype, such as a, b, d, e, or f. In some embodiments, the pharmaceutical composition comprises a plurality of saccharide-glycosphingolipid conjugates comprising saccharides from $H.$ $influenzae$ serotype d and at least one additional serotype, such as b, c, a, e, or f. In some embodiments, the pharmaceutical composition comprises a plurality of saccharide-glycosphingolipid conjugates comprising saccharides from $H.$ $influenzae$ serotype e and at least one additional serotype, such as b, c, d, a, or f. In some embodiments, the pharmaceutical composition comprises a plurality of saccharide-glycosphingolipid conjugates comprising saccharides from *H. influenzae* serotype f and at least one additional serotype comprising b, c, d, e, or a.

In some embodiments, the pharmaceutical composition comprises a plurality of saccharide-glycosphingolipid conjugates comprising saccharides from *H. influenzae* serotype a and serotype b. In some embodiments, the pharmaceutical composition comprises a plurality of saccharide-glycosphingolipid conjugates comprising saccharides from *H. influenzae* serotype a and serotype c. In some embodiments, the pharmaceutical composition comprises a plurality of saccharide-glycosphingolipid conjugates comprising saccharides from *H. influenzae* serotype a and serotype d. In some embodiments, the pharmaceutical composition comprises a plurality of saccharide-glycosphingolipid conjugates comprising saccharides from *H. influenzae* serotype a and serotype e. In some embodiments, the pharmaceutical composition comprises a plurality of saccharide-glycosphingolipid conjugates comprising saccharides from *H. influenzae* serotype a and serotype f. In some embodiments, the pharmaceutical composition comprises a plurality of saccharide-glycosphingolipid conjugates comprising saccharides from *H. influenzae* serotype a and any combination of saccharides from *H. influenzae* serotypes serotype b, c, d, e, and/or f.

The immunogenic saccharide-glycosphingolipid conjugate(s) can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition. In some embodiments, the pharmaceutical composition comprises a plurality of saccharide-carrier conjugates, wherein each of the saccharide carrier conjugates is present in the composition in equal amounts. In some embodiments, the pharmaceutical composition comprises a plurality of saccharide-carrier conjugates, wherein one or more of the saccharide carrier conjugates is present in the composition in a different amount. In some embodiments, each of the saccharide-carrier conjugate is present in the composition at an amount between about 0.001, 0.01, 0.1, 1, 2, 3, 4, 5, 6, 7, 8, 9, 10, 20, 30, 40, 50, 60, 70, 80, 90, 95, or 100%, by weight.

Any of the immunogenic saccharide-glycosphingolipid conjugate(s) described herein can include excipients that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition. Any of the immunogenic saccharide-glycosphingolipid conjugate(s) described herein can include adjuvants that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition.

In some embodiments, the pharmaceutical composition comprises a saccharide-lipid conjugate comprising a capsular polysaccharide or immunogenic fragment thereof from a serotype of *H. influenzae* conjugated to a lipid, and wherein the serotype is at least one of a, c, d, e, or f; or a combination thereof. In some embodiments, the pharmaceutical composition comprises a plurality of saccharide-lipid conjugates comprising at least 2, 3, 4, 5, 6, 7, 8, or 9 serotypes selected from the group consisting of a, b, c, d, e, and f. In some embodiments, the pharmaceutical composition comprises a plurality of saccharide-lipid conjugates comprising saccharides from *H. influenzae* serotype a and at least one additional serotype, such as b, c, d, e, or f. In some embodiments, the pharmaceutical composition comprises a plurality of saccharide-lipid conjugates comprising saccharides from *H. influenzae* serotype b and at least one additional serotype, such as a, c, d, e, or f. In some embodiments, the pharmaceutical composition comprises a plurality of saccharide-lipid conjugates comprising saccharides from *H. influenzae* serotype c and at least one additional serotype, such as b, a, d, e, or f. In some embodiments, the pharmaceutical composition comprises a plurality of saccharide-lipid conjugates comprising saccharides from *H. influenzae* serotype d and at least one additional serotype, such as b, c, a, e, or f. In some embodiments, the pharmaceutical composition comprises a plurality of saccharide-lipid conjugates comprising saccharides from *H. influenzae* serotype e and at least one additional serotype, such as b, c, d, a, or f. In some embodiments, the pharmaceutical composition comprises a plurality of saccharide-lipid conjugates comprising saccharides from *H. influenzae* serotype f and at least one additional serotype, such as b, c, d, e, or a.

In some embodiments, the pharmaceutical composition comprises a plurality of saccharide-lipid conjugates comprising saccharides from *H. influenzae* serotype a and serotype b. In some embodiments, the pharmaceutical composition comprises a plurality of saccharide-lipid conjugates comprising saccharides from *H. influenzae* serotype a and serotype c. In some embodiments, the pharmaceutical composition comprises a plurality of saccharide-lipid conjugates comprising saccharides from *H. influenzae* serotype a and serotype d. In some embodiments, the pharmaceutical composition comprises a plurality of saccharide-lipid conjugates comprising saccharides from *H. influenzae* serotype a and serotype e. In some embodiments, the pharmaceutical composition comprises a plurality of saccharide-lipid conjugates comprising saccharides from *H. influenzae* serotype a and serotype f. In some embodiments, the pharmaceutical composition comprises a plurality of saccharide-lipid conjugates comprising saccharides from *H. influenzae* serotype a and any combination of saccharides from *H. influenzae* serotypes serotype b, c, d, e, and/or f.

The immunogenic saccharide-lipid conjugate(s) can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition. In some embodiments, the pharmaceutical composition comprises a plurality of saccharide-carrier conjugates, wherein each of the saccharide carrier conjugates is present in the composition in equal amounts. In some embodiments, the pharmaceutical composition comprises a plurality of saccharide-carrier conjugates, wherein one or more of the saccharide carrier conjugates is present in the composition in a different amount. In some embodiments, each of the saccharide-carrier conjugate is present in the composition at an amount between about 0.001, 0.01, 0.1, 1, 2, 3, 4, 5, 6, 7, 8, 9, 10, 20, 30, 40, 50, 60, 70, 80, 90, 95, or 100%, by weight.

Any of the immunogenic saccharide-lipid conjugate(s) described herein can include excipients that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition. Any of the immunogenic saccharide-lipid conjugate(s) described herein can include adjuvants that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition.

Any pharmaceutical composition as described herein can be administered to one of a plurality of human subjects (e.g., a population of humans), which elicits at least one of the following side effects in less than about 5%, 10%, 20% or 30% of the plurality of humans: fatigue, headache, muscle pain, joint pain, decreased appetite, chills, or rash. In some embodiments, the pharmaceutical compositions described herein are formulated and/or administered to reduce the incidence of one or more side effects in a plurality of human subjects. In some embodiments, the amount of saccharide, amount of saccharide-carrier conjugate in the composition may be reduced to reduce one or more side effect associated with administration of the composition. In some embodiments, the dosage (e.g., the amount of saccharide, amount of saccharide-carrier conjugate) that is administered to the subject is reduced to reduce one or more side effect associated with administration of the composition. In some embodiments, the period of time between administration of dosage is increased to reduce one or more side effect associated with administration of the composition.

Also within the scope of the present disclosure are pharmaceutical compositions comprising a plurality of saccharide-carrier conjugates. In some embodiments, each of the carriers of a plurality of saccharide-carrier conjugates are polypeptides. In some embodiments, each of the carriers of a plurality of saccharide-carrier conjugates are glycosphingolipids. In some embodiments, each of the carriers of a plurality of saccharide-carrier conjugates are lipids. In some embodiments, the carriers of a plurality of saccharide-carrier conjugates are different. In some embodiments, the plurality of saccharide-carrier conjugates comprises polypeptides and glycosphingolipids. In some embodiments, the plurality of saccharide-carrier conjugates comprises polypeptides and lipids. In some embodiments, the plurality of saccharide-carrier conjugates comprises glycosphingolipids and lipids. In some embodiments, the plurality of saccharide-carrier conjugates comprises polypeptides, glycosphingolipids, and lipids.

In some embodiments, the pharmaceutical composition comprises immunogenic saccharide-polypeptide conjugates wherein the polypeptide is the same polypeptide in all the immunogenic saccharide-polypeptide conjugates. In some embodiments, the pharmaceutical composition comprises immunogenic saccharide-glycosphingolipid conjugates wherein the glycosphingolipid is the same glycosphingolipid in all the immunogenic saccharide-glycosphingolipid conjugates. In some embodiments, the pharmaceutical composition comprises immunogenic saccharide-lipid conjugates wherein the lipid is the same lipid in all the immunogenic saccharide-lipid conjugates.

In some embodiments, the pharmaceutical composition comprises immunogenic saccharide-polypeptide conjugates wherein the polypeptide(s) in the saccharide-polypeptide conjugates are a mixture of different polypeptide(s). In some embodiments, the pharmaceutical composition comprises immunogenic saccharide-glycosphingolipid conjugates wherein the glycosphingolipid(s) in the saccharide-glycosphingolipid conjugates are a mixture of different glycosphingolipid(s). In some embodiments, the pharmaceutical composition comprises immunogenic saccharide-lipid conjugates wherein the lipid(s) in the saccharide-lipid conjugates are a mixture of different lipid(s).

In some embodiments, the polypeptide of any of the plurality of saccharide-polypeptide conjugates can be the same polypeptide. For example, the polypeptide of any of the plurality of saccharide-polypeptide conjugates can be $CRM_{197}$. Alternatively, the plurality of saccharide-polypeptide conjugates can comprise a mixture of different polypeptides. For example, the plurality of saccharide-polypeptide conjugates can comprise a mixture of $CRM_{197}$, tetanus toxoid, and/or a diphtheria toxoid, or any fragment thereof.

In some embodiments, the glycosphingolipid of any of the plurality of saccharide-glycosphingolipid conjugates can be the same glycosphingolipid. For example, the glycosphingolipid of any of the plurality of saccharide-glycosphingolipid conjugates can be α-galactosylceramide or the lipid of any of the plurality of saccharide-lipid conjugates can be α-galactosylceramide. Alternatively, the plurality of saccharide-glycolipid conjugates can comprise a mixture of different glycolipids. For example, the plurality of saccharide-glycolipid conjugates can comprise a mixture of α-galactosylceramide, α-galactosylceramide analog, and/or OCH, or any fragment thereof.

In some embodiments, the lipid of any of the plurality of saccharide-lipid conjugates can be the same lipid. For example, the lipid of any of the plurality of saccharide-lipid conjugates can be α-galactosylceramide. Alternatively, the plurality of saccharide-lipid conjugates can comprise a mixture of different glycolipids. For example, the plurality of saccharide-lipid conjugates can comprise a mixture of α-galactosylceramide, α-galactosylceramide analog, and/or OCH, or any fragment thereof.

Any pharmaceutical composition described herein can be in unit dose form (unit dosage form). Any of the pharmaceutical compositions described herein may contain pharmaceutically acceptable concentrations of salts, buffering agents, preservatives, compatible carriers, adjuvants, and optionally other therapeutic agents.

Additionally, any of the pharmaceutical compositions described herein may further comprise an adjuvant. In some embodiments, the adjuvant can be an aluminum-cation comprises adjuvant. In other embodiments, the adjuvant can be aluminum phosphate, aluminum sulfate, or aluminum hydroxide. Additional non-limiting examples of suitable adjuvants for use in the pharmaceutical composition include: aluminum-based salts and variants thereof; emulsions (either water-in-oil or oil-in-water) and variants thereof, e.g., Freund's Incomplete Adjuvant, MF59® (Glaxosmithkline plc); PRR ligands and variants thereof, e.g., pathogen associated molecular patterns (PAMPs); TLR3 and RLR ligands or variants thereof, e.g., Synthetic analogs of dsRNA, poly (I:C), etc.; TLR4 ligands or variants thereof, e.g., bacterial flagellin, Glucopyranosyl Lipid Adjuvant (GLA), monophosphoryl lipid A, etc.; TLR5 ligands or variants thereof, e.g., imiquimod, gardiquimod, R848, etc.; TLR9 ligands or variants thereof, e.g., Oxydeoxynucleotides containing CpG motifs (CpG ODNs such as ODN1826 and ODN2006); NOD2 ligands or variants thereof, e.g., fragments of bacterial cell walls (such as muramyl dipeptide [MDP]); saponins including synthetic derivatives or variants thereof, e.g., QS21, TQL1055, etc.); or any combination of above.

Any of the pharmaceutical compositions described herein can further comprise an excipient, e.g., a pharmaceutically acceptable excipient. An excipient can be Acacia, Acesulfame Potassium, Acetic Acid, Glacial Acetone, Acetyltributyl Citrate, Acetyltriethyl Citrate, Agar, Albumin, Alcohol, Alginic Acid, Aliphatic Polyesters, Alitame, Almond Oil, Alpha Tocopherol, Aluminum Hydroxide Adjuvant, Aluminum Oxide, Aluminum Phosphate Adjuvant, Aluminum Stearate, Ammonia Solution, Ammonium Alginate, Ascorbic Acid, Ascorbyl Palmitate, Aspartame, Attapulgite, Bentonite, Benzalkonium Chloride, Benzethonium Chloride, Benzoic Acid, Benzyl Alcohol, Benzyl Benzoate, Boric Acid, Bronopol, Butylated Hydroxyanisole, Butylated Hydroxytoluene, Butylparaben, Calcium Alginate, Calcium Carbonate, Dibasic Anhydrous Calcium Phosphate, Dibasic Dihydrate Calcium Phosphate, Tribasic Calcium Phosphate, Calcium Stearate, Calcium Sulfate, Canola Oil, Carbomer, Carbon Dioxide, Carboxymethylcellulose Calcium, Carboxymethylcellulose Sodium, Carrageenan, Castor Oil, Hydrogenated Castor Oil, Microcrystalline Cellulose, Powdered Cellulose, Silicified Microcrystalline Cellulose, Cellulose Acetate, Cellulose Acetate Phthalate, Ceratonia, Cetostearyl Alcohol, Cetrimide, Cetyl Alcohol, Cetylpyridinium Chloride, Chitosan, Chlorhexidine, Chlorobutanol, Chlorocresol, Chlorodifluoroethane (HCFC), Chlorofluorocarbons (CFC), Chloroxylenol, Cholesterol, Citric Acid Monohydrate, Colloidal Silicon Dioxide, Coloring Agents, Copovidone, Corn Oil, Cottonseed Oil, Cresol, Croscarmellose Sodium, Crospovidone, Cyclodextrins, Cyclomethicone, Denatonium Benzoate, Dextrates, Dextrin, Dextrose, Dibutyl Phthalate, Dibutyl Sebacate, Diethanolamine, Diethyl Phthalate, Difluoroethane (HFC), Dimethicone, Dimethyl Ether, Dimethyl Phthalate, Dimethyl Sulfoxide, Dimethylacetamide, Disodium Edetate, Docusate Sodium, Edetic Acid, Erythorbic Acid, Erythritol, Ethyl Acetate, Ethyl Lactate, Ethyl Maltol, Ethyl Oleate, Ethyl Vanillin, Ethylcellulose, Ethylene Glycol Palmitostearate, Ethylene Vinyl Acetate, Ethylparaben, Fructose, Fumaric Acid, Gelatin, Glucose, Liquid, Glycerin, Glyceryl Behenate, Glyceryl Monooleate, Glyceryl Monostearate, Glyceryl Palmitostearate, Glycofurol, Guar Gum, Hectorite, Heptafluoropropane (HFC), Hexetidine, Hydrocarbons (HC), Hydrochloric Acid, Hydroxyethyl Cellulose, Hydroxyethylmethyl Cellulose, Hydroxypropyl Cellulose, Low-substituted Hydroxypropyl Cellulose, Hydroxypropyl Starch, Hypromellose, Hypromellose Acetate Succinate, Hypromellose Phthalate, Imidurea, Inulin, Iron Oxides, Isomalt, Isopropyl Alcohol, Isopropyl Myristate, Isopropyl Palmitate, Kaolin, Lactic Acid, Lactitol, Anhydrous Lactose, Monohydrate Lactose, Spray-Dried Lactose, Lanolin, Lanolin Alcohols, Hydrous Lanolin, Laurie Acid, Lecithin, Leucine, Linoleic Acid, Macrogol, Hydroxystearate Magnesium Aluminum Silicate, Magnesium Carbonate, Magnesium Oxide, Magnesium Silicate, Magnesium Stearate, Magnesium Trisilicate, Malic Acid, Maltitol, Maltitol Solution, Maltodextrin, Maltol, Maltose, Mannitol, Medium-chain Triglycerides, Meglumine, Menthol, Methylcellulose, Methylparaben, Mineral Oil, Light Mineral Oil, Mineral Oil and Lanolin Alcohols, Monoethanolamine, Monosodium Glutamate, Monothioglycerol, Myristic Acid, Neohesperidin Dihydrochalcone, Nitrogen, Nitrous Oxide, Octyldodecanol, Oleic Acid, Oleyl Alcohol, Olive Oil, Palmitic Acid, Paraffin, Peanut Oil, Pectin, Petrolatum, Petrolatum and Lanolin Alcohols, Phenol, Phenoxyethanol, Phenylethyl Alcohol, Phenylmercuric Acetate, Phenylmercuric Borate, Phenylmercuric Nitrate, Phosphoric Acid, Polacrilin Potassium, Poloxamer, Polycarbophil, Polydextrose, Polyethylene Glycol, Polyethylene Oxide, Polymethacrylates, Poly(methyl vinyl ether/maleic anhydride), Polyoxyethylene Alkyl Ethers, Polyoxyethylene Castor Oil Derivatives, Polyoxyethylene Sorbitan Fatty Acid Esters, Polyoxyethylene Stearates, Polyvinyl Acetate Phthalate, Polyvinyl Alcohol, Potassium Alginate, Potassium Benzoate, Potassium Bicarbonate, Potassium Chloride, Potassium Citrate, Potassium Hydroxide, Potassium Metabisulfite, Potassium Sorbate, Povidone, Propionic Acid, Propyl Gallate, Propylene Carbonate, Propylene Glycol, Propylene Glycol Alginate, Propylparaben, 2-Pyrrolidone, Raffinose, Saccharin, Saccharin Sodium, Saponite, Sesame Oil, Shellac, Simethicone, Sodium Acetate, Sodium Alginate, Sodium Ascorbate, Sodium Benzoate, Sodium Bicarbonate, Sodium Borate, Sodium Chloride, Sodium Citrate Dihydrate, Sodium Cyclamate, Sodium Hyaluronate, Sodium Hydroxide, Sodium Lactate, Sodium Lauryl Sulfate, Sodium Metabisulfite, Dibasic Sodium Phosphate, Monobasic Sodium Phosphate, Sodium Propionate, Sodium Starch Glycolate, Sodium Stearyl Fumarate, Sodium Sulfite, Sorbic Acid, Sorbitan Esters (Sorbitan Fatty Acid Esters), Sorbitol, Soybean Oil, Starch, Pregelatinized Starch, Sterilizable Maize Starch, Stearic Acid, Stearyl Alcohol, Sucralose, Sucrose, Compressible Sugar, Confectioner's Sugar, Sugar Spheres, Sulfobutylether b-Cyclodextrin, Sulfuric Acid, Sunflower Oil, Hard Fat Suppository Bases, Talc, Tartaric Acid, Tetrafluoroethane (HFC), Thaumatin, Thimerosal, Thymol, Titanium Dioxide, Tragacanth, Trehalose, Triacetin, Tributyl Citrate, Triethanolamine, Triethyl Citrate, Vanillin, Hydrogenated Vegetable Oil, Water, Anionic Emulsifying Wax, Carnauba Wax, Cetyl Esters Wax, Microcrystalline Wax, Nonionic Emulsifying Wax, White Wax, Yellow Wax, Xanthan Gum, Xylitol, Zein, Zinc Acetate, or Zinc Stearate.

Any of the pharmaceutical compositions described herein may further comprise a surfactant or emulsifier, or a combination thereof. A surfactant can be polysorbate, polymer glycol, a sorbitan ester, or any combination thereof. In some embodiments, polysorbate can be polysorbate 80. In other embodiments, polymer glycol can be polyethylene glycol. A pharmaceutical composition can comprise a specific polyethylene glycol based upon its molecular weight. A pharmaceutical composition can comprise a preservative.

Any of the pharmaceutical composition described herein may comprise a salt. The salt is an inorganic salt. A pharmaceutical composition can further comprise an antifungal compound or a salt thereof. An antifungal compound can be thimerosal, phenol, benzethonium chloride, or 2-phenoxyethanol.

Any of the pharmaceutical compositions described herein may further comprise a chelating agent. A chelating agent can be ethylenediainetetraacetic acid (EDTA).

Any of the pharmaceutical compositions described herein may further comprise a buffering agent. The buffering agent is succinate buffer agent, tris-acetate-ethylenediainetetraacetic acid (TAE) buffering agent, 4-(2-hydroxyethyl)-1-piperazineethanesulfonic acid (HEPES) buffering agent, phosphate buffering agent, sodium phosphate buffering agent, or a potassium phosphate buffering agent.

Any of the pharmaceutical composition may further comprise sterile water. When the pharmaceutical composition can be administered intramuscularly to a human, the pharmaceutical composition can elicit an immune response that lasts from about 1 week to about 30 years or longer.

In some embodiments, the pharmaceutical composition retains at least about 60% of its original biological activity when stored in a sealed container for about 24 months at a temperature of about 2° C.-8° C. when the sealed container is stored in an atmosphere having about 50% relative humidity and 1 atm of atmospheric pressure. In some embodiments, the pharmaceutical composition retains at least about 70% of its original biological activity when stored in a sealed container for about 24 months at a temperature of about 2° C.-8° C. when the sealed container is stored in an atmosphere having about 50% relative humidity and 1 atm of atmospheric pressure. In some embodiments, the pharmaceutical composition retains at least about 80% of its original biological activity when stored in a sealed container for about 24 months at a temperature of about 2° C.-8° C. when the sealed container is stored in an atmosphere having about 50% relative humidity and 1 atm of atmospheric pressure. In some embodiments, the pharmaceutical composition retains at least about 90% of its original biological activity when stored in a sealed container for about 24 months at a temperature of about 2° C.-8° C. when the sealed container is stored in an atmosphere having about 50% relative humidity and 1 atm of atmospheric pressure.

Any of the pharmaceutical composition described herein may be formulated for administration by a particular route. In some embodiments, the pharmaceutical composition is formulated for oral administration. In some embodiments, the pharmaceutical composition is formulated for rectal administration. In some embodiments, the pharmaceutical composition is formulated for administration by injection (e.g., intramuscular, subcutaneous).

Methods of Use

Aspects of the present disclosure provide methods, compositions, and kits for the prevention of H. influenzae infection. Aspects of the present disclosure provide methods, compositions, and kits for the inducing an immune response to H. influenzae, or one or more serotypes thereof. In some embodiments, the subject is at risk of H. influenzae infection, including risk of infection with one or more serotypes thereof. In some embodiments, the subject is at risk of exposure to H. influenzae, including risk of exposure to one or more serotypes thereof. In some embodiments, the subject lives in or is traveling to a geographic region in which one or more serotypes of H. influenzae are prevalent.

In one aspect, the disclosure provides methods, compositions, and kits for the prevention of H. influenzae infection in a subject. In one aspect, the disclosure provides methods, compositions, and kits for inducing an immune response to H. influenzae, or one or more serotypes thereof, in a subject. As used herein, "subject," "individual," and "patient" may be used interchangeably. A subject may be a mammal, such as a human or an animal. Mammals include, but are not limited to dog, cat, cow, horse, rat, mouse, sheep, monkey, and non-human primate. In some embodiments, the subject is a human.

In some embodiments, the subject is a human subject. In some embodiments, the subject is an adult. In some embodiments, the subject is a pediatric or neonatal subject. In general, pediatric subjects include infants, children, adolescents from 4 weeks up to the age of 18 years, whereas neonatal subjects are newborns less than about 4 weeks old. In some embodiments, the subject is child between the ages of 1-3 years, 3-5 years, 5-12 years. In some embodiments, the subject is an adolescent between the ages of 13-18 years. In some embodiments, the subject is an elderly subject (e.g., over the age of 65 years).

In some embodiments, the subject is at risk of exposure to and/or infection with H. influenzae. In some embodiments, the subject is at risk of exposure to and/or infection with one or more serotype of H. influenzae. In some embodiments, the subject lives in a geographic region in which one or more serotype of H. influenzae is prevalent. In some embodiments, the subject is traveling to a geographic region in which one or more serotype of H. influenzae is prevalent. For example, H. influenzae serotype a is prevalent in at least the United States (in particular, Alaska), Canada, Saudi Arabia, Australia, and Brazil. In some embodiments, the subject lives in or is traveling to the United States (in particular, Alaska), Canada, Saudi Arabia, Australia, or Brazil. In some embodiments, the subject is of an indigenous population of Canada or Alaska, also referred to as an Inuit.

Any of the methods or uses described herein may be for reducing or preventing H. influenzae infection in a subject or population of subject. As used herein, the terms "prevent," "prevention," and "preventing," include the administration of a composition to a subject to reduce, or delay the onset of the manifestation of clinical or subclinical symptoms, complications, pathologies or biochemical indicia of a disease or infection, or to reduce or inhibit the spread/transmission of H. influenzae. Such administration prior to infection, exposure, or risk of exposure to H. influenzae may be referred to as prophylactic administration. In some embodiments, the methods described herein are used to treat or prevent infection with H. influenzae. In some embodiments, the methods described herein are used to treat or prevent infection with one or more serotypes of H. influenzae (e.g., H. influenza serotype a, b, c, d, e, and/or f).

Any of the methods or uses described herein may be for reducing the severity of H. influenzae infection in a subject. As used herein, reducing the severity of H. influenzae infection encompasses reducing the severity of one or more symptoms of H. influenzae infection, reducing the duration of a H. influenzae infection, and/or slow or reverse the progression of the infection.

Any of the methods or uses described herein may be for the inducing an immune response to H. influenzae in a subject. In some embodiments, administration of the immunogenic saccharide-carrier conjugates described herein stimulates one or more immune responses in the subject. In some embodiments, administration of the immunogenic saccharide-carrier conjugates described herein stimulates one or more H. influenzae-specific immune responses. In some embodiments, administration of the immunogenic saccharide-carrier conjugates stimulates both T cell and B cell-dependent immune response. In some embodiments, administration of the immunogenic saccharide-carrier conjugates results in the production of enhanced levels of antibodies (e.g., high antibody titers) specific to H. influenzae, or a specific serotype thereof, and enhanced antibody functional activity (e.g., bacteriocidal activity, opsonophagocytic activity).

Methods of assessing an immune response stimulated by the immunogenic saccharide-conjugates described herein will be evident to one of ordinary skill in the art. For example, antibody levels may be assessed, for example in a biological sample from a subject (e.g., serum) by enzyme-linked immunosorbent assay (ELISA). Functional properties of antibodies may also be assessed a biological sample from a subject (e.g., serum) using methods known in the art, such as bacteriocidal assays, opsonophagocytosis assays, and/or antigen-binding assays.

Any of the compositions or pharmaceutical compositions described herein may be administered to a subject in a therapeutically effective amount or in a dose of a therapeutically effective amount. As used herein, a "therapeutically effective amount" of a composition is any amount that results in a desired response or outcome in a subject. For example, a therapeutically effective amount of a composition described herein can, in some embodiments, result in prevention of infection, induction of an immune response or an enhanced immune response to a H. influenzae, prevention or reduction of symptoms associated with a disease associated with H. influenzae, reduction of H. influenza bacterial load/burden, reduction of one or more symptoms associated with H. influenzae infection, and/or reduction of bacterial transmission or risk of transmission.

Combined with the teachings provided herein, by choosing among the various active compounds and weighing factors such as potency, relative bioavailability, subject body weight, subject age, state of the subject's immune system or immunological development, severity of adverse side-effects and preferred mode of administration, an effective prophylactic or therapeutic treatment regimen can be selected which does not cause substantial toxicity and yet is effective to induce a desired response in a particular subject.

Multiple doses per day, week or month may be contemplated to achieve appropriate systemic immune responses. In some embodiments, multiple doses are administered to achieve a desired level of antibodies described herein. In some embodiments, one or more doses of any of the pharmaceutical compositions described herein are administered to achieve a desired serum concnetraion of antibodies specific to *H. influenzae* saccharides. In some emboidments, administration of any of the pharmaceutical compositions described herein results in an antibody level of at least 0.1 µg/mL, 0.211 g/mL, 0.3 µg/mL, 0.4 µg/mL, 0.5 µg/mL, 0.6 µg/mL, 0.7 µg/mL, 0.8 µg/mL, 0.9 µg/mL, 1 µg/mL, 1.1 µg/mL, 1.2 µg/mL, 1.3 µg/mL, 1.4 mg/mL, 1.5 µg/mL, 1.61 µg/mL, 1.7 µg/mL, 1.8 µg/mL, 1.9 µg/mL, 2.0 µg/mL or higher. In general, titers of antibodies specific to *H. influenzae* serotype b saccharides of at least 1 µg/mL are considered to provide long term protection long term protection against infection with *H. influenzae* serotype b. See, e.g., Kayhty et al. *J. Infect. Dis.* (1983) 147:1100.

Determining a therapeutically effective amount specifically depends on such factors as toxicity and efficacy of the medicament. Toxicity may be determined using methods well known in the art. Efficacy may be determined utilizing the same guidance. A pharmaceutically effective amount, therefore, is an amount that is deemed by the clinician to be toxicologically tolerable, yet efficacious. Efficacy can be measured for example, by quantifying antibody titers (e.g., specific anti-saccharide antibodies) in the subject (or biological a sample obtained from the subject), assessing antibody activity (e.g., bacteriocidal activity, opsonophagocytic activity), and/or monitoring the incidence of infection.

In some embodiments, a therapeutically effective amount of any of the pharmaceutical compositions described herein is administered in a single dose. In some embodiments, a therapeutically effective amount of any of the pharmaceutical compositions described herein is administered in to the subject in multiple doses. In some embodiments, the methods described herein involve administering one or more doses of any of the pharmaceutical compositions to the subject. In some embodiments, the methods described herein involve concomitant administration of the multiples doses of any of the pharmaceutical compositions to the subject. In some embodiments, the subject may be administered one dose of any of the pharmaceutical compositions described herein followed by one or more additional doses (e.g., boosters) after an interval of time. In some embodiments, the subject may be administered one dose of any of the pharmaceutical compositions described herein followed by one or more additional doses (e.g., boosters) after at least 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, 36 months, or longer.

As described herein, any of the saccharide-carrier conjugates described herein may be formulated for prophylactic use (e.g., as a vaccine). In some embodiments, the saccharide-polypeptide conjugates as described herein can be formulated for use in a vaccine. pharmaceutical compositions comprising a saccharide-polypeptide conjugate as described herein can be formulated for use in a vaccine. In some embodiments, the pharmaceutical compositions comprising a saccharide-polypeptide conjugate as described herein can be used in a vaccine. In some embodiments, the saccharide-glycosphingolipid conjugates as described herein can be formulated for use in a vaccine. In some embodiments, the pharmaceutical compositions comprising a saccharide-glycosphingolipid conjugate as described herein can be formulated for use in a vaccine. In some embodiments, the pharmaceutical compositions comprising a saccharide-glycosphingolipid conjugate as described herein can be used in a vaccine. In some embodiments, the saccharide-lipid conjugates as described herein can be formulated for use in a vaccine. In some embodiments, the pharmaceutical compositions comprising a saccharide-lipid conjugate as described herein can be formulated for use in a vaccine. In some embodiments, the pharmaceutical compositions comprising a saccharide-lipid conjugate as described herein can be used in a vaccine.

In some embodiments, the vaccine can be administered to a subject. In some embodiments, the subject can be a human. In some embodiments, the subject (e.g., human) can be a subject or human in need thereof. In some embodiments, the subject is at risk of *H. influenzae* infection. In some embodiments, the subject is at risk of infection with *H. influenzae* serotype a. In some embodiments, the subject is at risk of infection with *H. influenzae* serotype b. In some embodiments, the subject is at risk of infection with *H. influenzae* serotype c. In some embodiments, the subject is at risk of infection with *H. influenzae* serotype d. In some embodiments, the subject is at risk of infection with *H. influenzae* serotype e. In some embodiments, the subject is at risk of infection with *H. influenzae* serotype f. In some embodiments, the subject is at risk of infection with more than one *H. influenzae* serotype, such as serotype a, b, c, d, e, and/or f. In some embodiments, the saccharide-polypeptide conjugate is administered by intramuscular injection. In some embodiments, the saccharide-polypeptide conjugate is administered via intramuscular, intraperitoneal, intradermal or subcutaneous routes, or via mucosal administration to the oral/alimentary, respiratory or genitourinary tracts. In some embodiments, the saccharide-polypeptide conjugate is administered via a suppository. In some embodiments, the saccharide-polypeptide conjugate is administered intranasally.

In some embodiments, the pharmaceutical composition comprising a saccharide-polypeptide conjugate is administered by intramuscular injection. In some embodiments, the pharmaceutical composition comprising a saccharide-polypeptide conjugate is administered via intramuscular, intraperitoneal, intradermal or subcutaneous routes, or via mucosal administration to the oral/alimentary, respiratory or genitourinary tracts. In some embodiments, the pharmaceutical composition comprising a saccharide-polypeptide conjugate is administered intranasally.

In some embodiments, the pharmaceutical composition is administered intramuscularly and elicits an immune response that lasts from 1 week to 30 years or longer.

In some embodiments, the saccharide-glycosphingolipid conjugate is be administered by intramuscular injection. In some embodiments, the saccharide-glycosphingolipid conjugate is administered via intramuscular, intraperitoneal, intradermal or subcutaneous routes, or via mucosal administration to the oral/alimentary, respiratory or genitourinary tracts. In some embodiments, the saccharide-glycosphingolipid conjugate is administered via a suppository. In some embodiments, the saccharide-glycosphingolipid conjugate is administered intranasally.

In some embodiments, the pharmaceutical composition comprising a saccharide-glycosphingolipid conjugate is administered by intramuscular injection. In some embodiments, the pharmaceutical composition comprising a saccharide-glycosphingolipid conjugate is administered via intramuscular, intraperitoneal, intradermal or subcutaneous routes, or via mucosal administration to the oral/alimentary, respiratory or genitourinary tracts. In some embodiments, the pharmaceutical composition comprising a saccharide-glycosphingolipid conjugate is administered intranasally.

In some embodiments, the pharmaceutical composition is administered intramuscularly and elicits an immune response that lasts from 1 week to 30 years or longer.

In some embodiments, the saccharide-lipid conjugate is administered by intramuscular injection. In some embodiments, the saccharide-lipid conjugate is administered via intramuscular, intraperitoneal, intradermal or subcutaneous routes, or via mucosal administration to the oral/alimentary, respiratory or genitourinary tracts. In some embodiments, the saccharide-lipid conjugate is administered via a suppository. In some embodiments, the saccharide-lipid conjugate is administered intranasally.

In some embodiments, the pharmaceutical composition comprising a saccharide-lipid conjugate is administered by intramuscular injection. In some embodiments, the pharmaceutical composition comprising a saccharide-lipid conjugate is administered via intramuscular, intraperitoneal, intradermal or subcutaneous routes, or via mucosal administration to the oral/alimentary, respiratory or genitourinary tracts. In some embodiments, the pharmaceutical composition comprising a saccharide-lipid conjugate is administered intranasally. In some embodiments, the pharmaceutical composition is administered intramuscularly and elicits an immune response that lasts from 1 week to 30 years, or longer.

In general, the duration of an immune response may be assessed, for example, by evaluating the immune response in the subject (e.g., biological sample(s) obtained from the subject) over a period of time. In some embodiments, if the magnitude of the immune response is reduced (or absent) in the subject as compared to the magnitude of the immune response in the subject at a prior time, the immune response may be determined to have terminated. In some embodiments, if the magnitude of the immune response is below a threshold (or absent) in the subject, the immune response may be determined to have terminated. In some embodiments, the immune response is assessed by quantifying the number of antibodies (e.g., saccharide-specific antibodies), activity of antibodies, or the number and/or activity of effector and/or memory cells. In some embodiments, the pharmaceutical composition is administered intramuscularly and can elicit an immune response that lasts (is detectable) for at least 1 week, 2 weeks, 3 weeks, 4 weeks, 1 month, 2 month, 3 month, 4 month, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, or longer.

The pharmaceutical compositions described herein, including vaccines, may be monovalent (containing saccharide-polypeptide conjugate comprising saccharides from one serotype of *H. influenzae*) or multivalent (containing saccharide-polypeptide conjugate comprising saccharides from more than one serotype of *H. influenzae*). In some embodiments, the pharmaceutical composition is monovalent and comprises a saccharide-polypeptide conjugate comprising a capsular polysaccharide or immunogenic fragment thereof from one serotype of *H. influenzae* (e.g., serotype a, b, c, d, e, or f) conjugated to a polypeptide. In some embodiments, the pharmaceutical composition is multivalent and comprises a saccharide-polypeptide conjugate comprising a capsular polysaccharide or immunogenic fragment thereof from more than one serotype (e.g., 2, 3, 4, 5, or 6) of *H. influenzae* (e.g., serotype a, b, c, d, e, or f) conjugated to a polypeptide.

For example, a pharmaceutical composition administered to a subject can comprise a saccharide-polypeptide conjugate comprising a capsular polysaccharide or immunogenic fragment thereof from a serotype of *H. influenzae* conjugated to a polypeptide, the serotype is a, c, d, e, or f; or a combination thereof. A pharmaceutical composition administered to a subject can comprise a saccharide-polypeptide conjugate comprising a capsular polysaccharide or immunogenic fragment thereof from a serotype of *H. influenzae* conjugated to a polypeptide, the serotype is a, and at least one of b, c, d, e, or f; or a combination thereof. A pharmaceutical composition administered to a subject can comprise a saccharide-polypeptide conjugate comprising a capsular polysaccharide or immunogenic fragment thereof from a serotype of *H. influenzae* conjugated to a polypeptide, the serotype is b, and at least one of a, c, d, e, or f; or a combination thereof. A pharmaceutical composition administered to a subject can comprise a saccharide-polypeptide conjugate comprising a capsular polysaccharide or immunogenic fragment thereof from a serotype of *H. influenzae* conjugated to a polypeptide, the serotype is c, and at least one of b, a, d, e, or f; or a combination thereof. A pharmaceutical composition administered to a subject can comprise a saccharide-polypeptide conjugate comprising a capsular polysaccharide or immunogenic fragment thereof from a serotype of *H. influenzae* conjugated to a polypeptide, the serotype is d, and at least one of b, c, a, e, or f; or a combination thereof. A pharmaceutical composition administered to a subject can comprise a saccharide-polypeptide conjugate comprising a capsular polysaccharide or immunogenic fragment thereof from a serotype of *H. influenzae* conjugated to a polypeptide, the serotype is e, and at least one of b, c, d, a, or f; or a combination thereof. A pharmaceutical composition administered to a subject can comprise a saccharide-polypeptide conjugate comprising a capsular polysaccharide or immunogenic fragment thereof from a serotype of *H. influenzae* conjugated to a polypeptide, the serotype is f, and at least one of b, c, d, e, or a; or a combination thereof.

As another example, a pharmaceutical composition administered to a subject can comprise a saccharide-glycosphingolipid conjugate comprising a capsular polysaccharide or immunogenic fragment thereof from a serotype of *H. influenzae* conjugated to a glycosphingolipid, the serotype is a, c, d, e, or f; or a combination thereof. A pharmaceutical composition administered to a subject can comprise a saccharide-glycosphingolipid conjugate comprising a capsular polysaccharide or immunogenic fragment thereof from a serotype of *H. influenzae* conjugated to a glycosphingolipid, the serotype is a, and at least one of b, c, d, e, or f; or a combination thereof. A pharmaceutical composition administered to a subject can comprise a saccharide-glycosphingolipid conjugate comprising a capsular polysaccharide or immunogenic fragment thereof from a serotype of *H. influenzae* conjugated to a glycosphingolipid, the serotype is b, and at least one of a, c, d, e, or f; or a combination thereof. A pharmaceutical composition administered to a subject can comprise a saccharide-glycosphingolipid conjugate comprising a capsular polysaccharide or immunogenic fragment thereof from a serotype of *H. influenzae* conjugated to a glycosphingolipid, the serotype is c, and at least one of b, a, d, e, or f; or a combination thereof. A pharmaceutical composition administered to a subject can comprise a saccharide-glycosphingolipid conjugate comprising a capsular polysaccharide or immunogenic fragment thereof from a serotype of *H. influenzae* conjugated to a glycosphingolipid, the serotype is d, and at least one of b, c, a, e, or f; or a combination thereof. A pharmaceutical composition administered to a subject can comprise a saccharide-glycosphingolipid conjugate comprising a capsular polysaccharide or immunogenic fragment thereof from a serotype of *H. influenzae* conjugated to a glycosphingolipid, the serotype is e, and at least one of b, c, d, a, or f; or a combination thereof. A pharmaceutical composition administered to a subject can comprise a saccharide-glycosphingolipid conjugate comprising a capsular polysaccharide or immunogenic fragment thereof from a serotype of *H. influenzae* conjugated to a glycosphingolipid, the serotype is f, and at least one of b, c, d, e, or a; or a combination thereof.

As an additional example, a pharmaceutical composition administered to a subject can comprise a saccharide-lipid conjugate comprising a capsular polysaccharide or immunogenic fragment thereof from a serotype of *H. influenzae* conjugated to a lipid, the serotype is a, c, d, e, or f; or a combination thereof. A pharmaceutical composition administered to a subject can comprise a saccharide-lipid conjugate comprising a capsular polysaccharide or immunogenic fragment thereof from a serotype of *H. influenzae* conjugated to a lipid, the serotype is a, and at least one of b, c, d, e, or f; or a combination thereof. A pharmaceutical composition administered to a subject can comprise a saccharide-lipid conjugate comprising a capsular polysaccharide or immunogenic fragment thereof from a serotype of *H. influenzae* conjugated to a lipid, the serotype is b, and at least one of a, c, d, e, or f; or a combination thereof. A pharmaceutical composition administered to a subject can comprise a saccharide-lipid conjugate comprising a capsular polysaccharide or immunogenic fragment thereof from a serotype of *H. influenzae* conjugated to a lipid, the serotype is c, and at least one of b, a, d, e, or f; or a combination thereof. A pharmaceutical composition administered to a subject can comprise a saccharide-lipid conjugate comprising a capsular polysaccharide or immunogenic fragment thereof from a serotype of *H. influenzae* conjugated to a lipid, the serotype is d, and at least one of b, c, a, e, or f; or a combination thereof. A pharmaceutical composition administered to a subject can comprise a saccharide-lipid conjugate comprising a capsular polysaccharide or immunogenic fragment thereof from a serotype of *H. influenzae* conjugated to a lipid, the serotype is e, and at least one of b, c, d, a, or f; or a combination thereof. A pharmaceutical composition administered to a subject can comprise a saccharide-lipid conjugate comprising a capsular polysaccharide or immunogenic fragment thereof from a serotype of *H. influenzae* conjugated to a lipid, the serotype is f, and at least one of b, c, d, e, or a; or a combination thereof.

As discussed herein, different serotypes of *H. influenzae* may be more pervasive in different geographical areas. Additionally, the prevalence of specific *H. influenzae* serotypes in a geographic region may evolve. See, e.g., Tsang et al. *Lancet Infect. Dis.* (2008) 8:737. For example, *H. influenzae* serotype a has been found to cause *H. influenzae* disease in the United States, Canada, Saudi Arabia, and Australia. Therefore, administration of a pharmaceutical composition comprising a saccharide-polypeptide conjugate comprising saccharides from *H. influenzae* serotype a may improve protection against *H. influenzae* disease in subjects in the United States, Canada, Saudi Arabia, and/or Australia. Administration of a pharmaceutical composition comprising a saccharide-glycosphingolipid conjugate comprising saccharides from *H. influenzae* serotype a may improve protection against *H. influenzae* disease in subjects in the United States, Canada, Saudi Arabia, and/or Australia. Administration of a pharmaceutical composition comprising a saccharide-lipid conjugate comprising saccharides from *H. influenzae* serotype a may improve protection against *H. influenzae* disease in the subject in the United States, Canada, Saudi Arabia, and/or Australia.

Furthermore, administration of a pharmaceutical composition comprising a saccharide-polypeptide conjugate comprising saccharides from *H. influenzae* serotype a and serotype b may improve protection against *H. influenzae* disease in the subject in the United States, Canada, Saudi Arabia, and/or Australia. Administration of a pharmaceutical composition comprising a saccharide-glycosphingolipid conjugate comprising saccharides from *H. influenzae* serotype a and serotype b may improve protection against *H. influenzae* disease in subjects in the United States, Canada, Saudi Arabia, and/or Australia. Administration of a pharmaceutical composition comprising a saccharide-lipid conjugate comprising saccharides of *H. influenzae* serotype a and serotype b may improve protection against *H. influenzae* disease in subjects in the United States, Canada, Saudi Arabia, and/or Australia.

*H. influenzae* serotypes d, e, and f have been found to cause *H. influenzae* disease in Australia, and Europe. For example in Europe, *H. influenzae* serotypes d, e, and f have been found to cause *H. influenzae* disease in Spain, England, and Wales. Therefore, administration of a pharmaceutical composition comprising a saccharide-polypeptide conjugate comprising saccharides from *H. influenzae* serotype d may improve protection against *H. influenzae* disease in subjects in Australia and/or Europe. Administration of a pharmaceutical composition comprising a saccharide-glycosphingolipid conjugate comprising saccharides from *H. influenzae* serotype d may improve protection against *H. influenzae* disease in subjects in Australia and/or Europe. Administration of a pharmaceutical composition comprising a saccharide-lipid conjugate comprising the saccharides from *H. influenzae* serotype d may improve protection against *H. influenzae* disease in subjects in Australia and/or Europe. Furthermore, administration of a pharmaceutical composition comprising a saccharide-polypeptide conjugate comprising saccharides from *H. influenzae* serotype d and serotype b may improve protection against *H. influenzae* disease in subjects in Australia and/or Europe. Administration of a pharmaceutical composition comprising a saccharide-glycosphingolipid conjugate comprising saccharides from *H. influenzae* serotype d and serotype b may improve protection against *H. influenzae* disease in subjects in Australia and/or Europe. Administration of a pharmaceutical composition comprising a saccharide-lipid conjugate comprising saccharides from *H. influenzae* serotype d and serotype b may improve protection against *H. influenzae* disease in subjects in Australia and/or Europe. Additionally, administration of a pharmaceutical composition comprising a saccharide-polypeptide conjugate comprising saccharides from *H. influenzae* serotype e may improve protection against *H. influenzae* disease in subjects in Australia and/or Europe. Administration of a pharmaceutical composition comprising a saccharide-glycosphingolipid conjugate comprising saccharides from *H. influenzae* serotype e may improve protection against *H. influenzae* disease in subjects in Australia and/or Europe. Administration of a pharmaceutical composition comprising a saccharide-lipid conjugate comprising saccharides from *H. influenzae* serotype e may improve protection against *H. influenzae* disease in subjects in Australia and/or Europe. Furthermore, administration of a pharmaceutical composition comprising a saccharide-polypeptide conjugate comprising saccharides from *H. influenzae* serotype e and serotype b may improve protection against *H. influenzae* disease in subjects in Australia and/or Europe. Administration of a pharmaceutical composition comprising a saccharide-glycosphingolipid conjugate comprising saccharides from *H. influenzae* serotype e and serotype b may improve protection against *H. influenzae* disease in subjects in the Australia and/or Europe. Administration of a pharmaceutical composition comprising a saccharide-lipid conjugate comprising saccharides from *H. influenzae* serotype e and serotype b may improve protection against *H. influenzae* disease in subjects in the Australia and/or Europe. Additionally, administration of a pharmaceutical composition comprising a saccharide-polypeptide conjugate comprising saccharides from *H. influenzae* serotype f may improve protection against *H. influenzae* disease in subjects in Australia and/or Europe. Administration of a pharmaceutical composition comprising a saccharide-glycosphingolipid conjugate comprising saccharides from *H. influenzae* serotype f may improve protection against *H. influenzae* disease in subjects in Australia and/or Europe. Administration of a pharmaceutical composition comprising a saccharide-lipid conjugate comprising saccharides from *H. influenzae* serotype f may improve protection against *H. influenzae* disease in subjects in Australia and/or Europe. Furthermore, administration of a pharmaceutical composition comprising a saccharide-polypeptide conjugate comprising saccharides from *H. influenzae* serotype f and serotype b may improve protection against *H. influenzae* disease in subjects in Australia and/or Europe. Administration of a pharmaceutical composition comprising a saccharide-glycosphingolipid conjugate comprising saccharides from *H. influenzae* serotype f and serotype b may improve protection against *H. influenzae* disease in subjects in Australia and/or Europe. Administration of a pharmaceutical composition comprising a saccharide-lipid conjugate comprising saccharides from *H. influenzae* serotype f and serotype b may improve protection against *H. influenzae* disease in subjects in Australia and/or Europe. Administration of a pharmaceutical composition comprising a saccharide-polypeptide conjugate comprising saccharides from *H. influenzae* serotype d, serotype e, and serotype f may improve protection against *H. influenzae* disease in subjects in Australia and/or Europe. Administration of a pharmaceutical composition comprising a saccharide-glycosphingolipid conjugate comprising saccharides from *H. influenzae* serotype d, serotype e, and serotype f may improve protection against *H. influenzae* disease in subjects in Australia and/or Europe. Administration of a pharmaceutical composition comprising a saccharide-lipid conjugate comprising saccharides from *H. influenzae* serotype d, serotype e, and serotype f may improve protection against *H. influenzae* disease in subjects in Australia and/or Europe. Furthermore, administration of a pharmaceutical composition comprising a saccharide-polypeptide conjugate comprising saccharides from *H. influenzae* serotype d, serotype e, serotype f and serotype b may improve protection against *H. influenzae* disease in subjects in Australia and/or Europe. Administration of a pharmaceutical composition comprising a saccharide-glycosphingolipid conjugate comprising saccharides from *H. influenzae* serotype d, serotype e, serotype f and serotype b may improve protection against *H. influenzae* disease in subjects in Australia and/or Europe. Administration of a pharmaceutical composition comprising a saccharide-lipid conjugate comprising saccharides from *H. influenzae* serotype d, serotype e, serotype f and serotype b may improve protection against *H. influenzae* disease in subjects in Australia and/or Europe.

Also, *H. influenzae* serotypes a, d, e, and f have been found to cause *H. influenzae* disease in Australia. Therefore, administration of a pharmaceutical composition comprising a saccharide-polypeptide conjugate comprising saccharides from *H. influenzae* serotype a, serotype d, serotype e, and serotype f may improve protection against *H. influenzae* disease in subjects in Australia. Administration of a pharmaceutical composition comprising a saccharide-glycosphingolipid conjugate comprising saccharides from *H. influenzae* serotype a, serotype d, serotype e, and serotype f may improve protection against *H. influenzae* disease in subjects in Australia. Administration of a pharmaceutical composition comprising a saccharide-lipid conjugate comprising saccharides from *H. influenzae* serotype a, serotype d, serotype e, and serotype f may improve protection against *H. influenzae* disease in subjects in Australia. Furthermore, administration of a pharmaceutical composition comprising a saccharide-polypeptide conjugate comprising saccharides from *H. influenzae* serotype a, serotype d, serotype e, and serotype f may improve protection against *H. influenzae* disease in subjects in Australia. Administration of a pharmaceutical composition comprising a saccharide-glycosphingolipid conjugate comprising saccharides from *H. influenzae* serotype a, serotype d, serotype e, and serotype f may improve protection against *H. influenzae* disease in subjects in Australia. Administration of a pharmaceutical composition comprising a saccharide-lipid conjugate comprising saccharides from *H. influenzae* serotype a, serotype d, serotype e, and serotype f may improve protection against *H. influenzae* disease in subjects in Australia.

Additionally, different *H. influenzae* serotypes can be more pervasive and cause disease among some populations of indigenous peoples. Indigenous peoples can refer to a population comprising at least about: 1%, 5%, 10%, 25%, 50%, 75%, or 100% of indigenous individuals. The term "indigenous individual" may refer to a person with at least 10%, 15%, 20%, 25%, 50%, 75%, or 100% indigenous genetic heritage. For example, invasive clinical disease caused by (or associated with) *H. influenzae* serotype a can be found in indigenous peoples of the Canadian north (e.g., Keewitan region of Nunavut) and Alaska, the southwestern United States, Australia, and Saudi Arabia (e.g., in Berbers of Saudi Arabia). Invasive clinical disease caused by (or associated with) *H influenzae* serotype d, serotype e, and serotype f can be found in indigenous peoples of Spain and Australia, and peoples of Norse or Viking descent in England and Wales. Therefore, administration of a vaccine may improve protection against *H. influenzae*, or specific serotypes of *H. influenzae*, in an indigenous individual and among an indigenous population. For example, administration of a pharmaceutical composition comprising a saccharide-polypeptide conjugate comprising saccharides from *H. influenzae* serotype a, serotype b, serotype c, serotype d, serotype e, and/or serotype f to an indigenous individual may improve protection against *H. influenzae* disease in the indigenous individual. Administration of a pharmaceutical composition comprising a saccharide-glycosphingolipid conjugate comprising saccharides from *H. influenzae* serotype a, serotype b, serotype c, serotype d, serotype e, and/or serotype f to an indigenous individual may improve protection against *H. influenzae* disease in the indigenous individual. Administration of a pharmaceutical composition comprising a saccharide-lipid conjugate comprising saccharides from *H. influenzae* serotype a, serotype b, serotype c, serotype d, serotype e, and/or serotype f to an indigenous individual may improve protection against *H. influenzae* disease in the indigenous individual.

In other embodiments, the conducting of any of the methods described herein may not result in more than about: 50%, 40%, 30%, 20%, 10%, 5%, 4%, 3%, 2%, or 1% suppression of an immunity conveyed by a first vaccine containing an immunogenic saccharide-polypeptide conjugate, as measured by antibody response to the saccharide of the immunogenic saccharide-polypeptide conjugate, wherein the antibody response is measured by measuring antibody titers.

Saccharide-carrier Conjugate Kits

Also within the scope of the present disclosure are kits for use in the methods described herein. The saccharide-polypeptide conjugates and pharmaceutical compositions described herein can be contained in a kit. Such kits may include one or more containers comprising saccharide-carrier conjugates. In some embodiments, the kit may further comprise instructions for use, including, for example information as to the amount of one or more components, suitable conditions for administering one or more component to a subject. The kit may further comprise a description of selecting a subject suitable for administration based on identifying whether that subject is at risk for exposure to *H. influenzae* or contracting a *H. influenzae* infection. In still other embodiments, the instructions comprise a description of administering a composition containing the saccharide-carrier conjugates a subject at risk of exposure to *H. influenzae* or contracting *H. influenzae* infection.

In some embodiments, the saccharide-polypeptide conjugates are contained in a kit. In some embodiments, the saccharide-polypeptide conjugates and/or pharmaceutical compositions are stored in a container. In some embodiments, the container is a syringe. In some embodiments, the container is a vial. In some embodiments, the container is a vial with a rubber septum or a septum made of flexible, reclose-able material.

In some embodiments, the saccharide-glycosphingolipid conjugates and pharmaceutical compositions described herein are contained in a kit. In some embodiments, the kit can further comprise instructions for use. In some embodiments, the saccharide-glycosphingolipid conjugates and/or pharmaceutical compositions can be stored in a container. In some embodiments, the container is a syringe. In some embodiments, the container is a vial. In some embodiment, the container is a vial with a rubber septum or a septum made of flexible, reclose-able material.

In some embodiments, the saccharide-lipid conjugates and pharmaceutical compositions described herein are contained in a kit. In some embodiments, the kit can further comprise instructions for use. In some embodiments, the saccharide-lipid conjugates and/or pharmaceutical compositions are stored in a container. In some embodiments, the container is a syringe. In some embodiments, the container is a vial. In some embodiments, the container is a vial with a rubber septum or a septum made of flexible, reclose-able material.

Any of the containers may contain a single dose of saccharide-carrier conjugates. Alternatively, any of the containers may be multi-dose containers and contain more than one dose of saccharide-carrier conjugates.

The components of the kit may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or packages insert may indicate that the kit is used, for example, to induce an immune response in a subject and/or provide protection to the subject from subsequent infection with a *H. influenzae* infection. Instructions may be provided for practicing any of the methods described herein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

The following examples are included to further describe some aspects of the present disclosure, and should not be used to limit the scope of the embodiments described herein.

Example 1

Method of Vaccination for Children Age Two Years or Under

This example shows vaccine compositions and a dosing schedule for the vaccine compositions for children age two years or under. An aqueous vaccine composition is composed of an immunogenic saccharide-polypeptide conjugate containing capsular polysaccharides from the *H. influenzae* serotype a. The aqueous vaccine is formulated to contain from 1-5 microgram of each serotype and aluminum phosphate as an adjuvant.

A single 0.5 mL dose of an aqueous vaccine is given by intramuscular injection to a child age two years or under at three or four different times. A single dose is given at an age of at least 6 weeks. A single dose is given at age 4 months. Optionally, a single dose is given at 6 months or older. A single dose given at age 12 through 24 months.

Example 2

Method of Vaccination for Children Ages 2 Through 17 Years Old

This example shows vaccine compositions and a dosing schedule for the vaccine compositions for children ages 2 through 18 years old. An aqueous vaccine composition is composed of an immunogenic saccharide-polypeptide conjugate containing capsular polysaccharides from the *H. influenzae* serotype a. The aqueous vaccine is formulated to contain from 1-5 microgram of each serotype and aluminum phosphate as an adjuvant.

A single 0.5 mL dose of the aqueous vaccine is given by intramuscular injection to a child who is age 2 through 18 years old.

Example 3

Composition and Method of Use of a Vaccination for Protection Against *H. influenzae* in the United States, Canada, Saudi Arabia, and Australia This example shows a vaccine composition that provides protection against *H. influenzae* for subjects in the United States, Canada, Saudi Arabia, and Australia. An aqueous vaccine composition is composed of an immunogenic saccharide-polypeptide conjugate containing capsular polysaccharides from the *H. influenzae* serotype a. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease found in the United States, Canada, Saudi Arabia, and Australia is improved.

Example 4

Composition and Method of Use of a Vaccination for Protection Against *H. influenzae* in Europe and Australia This example shows a vaccine composition that provides protection against *H. influenzae* for subjects in the Europe and Australia. An aqueous vaccine composition is composed of an immunogenic saccharide-polypeptide conjugate containing capsular polysaccharides from the *H. influenzae* serotype d, e, and f. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease found in the Europe and Australia is improved.

Example 5

Composition and Method of Use of a Vaccination for Protection Against *H. influenzae* in Australia This example shows a vaccine composition that provides protection against *H. influenzae* for subjects in Australia. An aqueous vaccine composition is composed of an immunogenic saccharide-polypeptide conjugate containing capsular polysaccharides from the *H. influenzae* serotype a, d, e, and f. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease found in Australia is improved.

Example 6

Composition and Method of Use of a Vaccination for Protection Against *H. influenzae* Serotype a This example shows a vaccine composition that provides protection against *H. influenzae*. An aqueous vaccine composition is composed of an immunogenic saccharide-polypeptide conjugate containing capsular polysaccharides from the *H. influenzae* serotype a. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 7

Composition and Method of Use of a Vaccination for Protection Against *H. influenzae* Serotype c This example shows a vaccine composition that provides protection against *H. influenzae*. An aqueous vaccine composition is composed of an immunogenic saccharide-polypeptide conjugate containing capsular polysaccharides from the *H. influenzae* serotype a. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 8

Composition and Method of Use of a Vaccination for Protection Against *H. influenzae* Serotype d This example shows a vaccine composition that provides protection against *H. influenzae*. An aqueous vaccine composition is composed of an immunogenic saccharide-polypeptide conjugate containing capsular polysaccharides from the *H. influenzae* serotype a. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 9

Composition and Method of Use of a Vaccination for Protection Against *H. influenzae* Serotype e This example shows a vaccine composition that provides protection against *H. influenzae*. An aqueous vaccine composition is composed of an immunogenic saccharide-polypeptide conjugate containing capsular polysaccharides from the *H. influenzae* serotype a. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 10

Composition and Method of Use of a Vaccination for Protection Against *H. influenzae* Serotypes a, b, c, d, e, and f This example shows a vaccine composition that provides protection against *H. influenzae*. An aqueous vaccine composition is composed of an immunogenic saccharide-polypeptide conjugate containing capsular polysaccharides from the *H. influenzae* serotype a, b, c, d, e, and f. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 11

Composition and Method of Use of a Vaccination for Protection Against *H. influenzae* Serotypes a and b This example shows a vaccine composition that provides protection against *H. influenzae*. An aqueous vaccine composition is composed of an immunogenic saccharide-polypeptide conjugate containing capsular polysaccharides from the *H. influenzae* serotypes a and b. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 12

Method of Making a Saccharide-Polypeptide Conjugate Pharmaceutical Composition

This example shows a method of making a saccharide-polypeptide conjugate pharmaceutical composition. A capsular polysaccharide is isolated from a *H. influenzae* serotype a. The serotype a capsular polysaccharide is conjugated to a $CRM_{197}$ polypeptide. The saccharide-polypeptide conjugate is contacted with an excipient.

Example 13

Method of Making a Saccharide-Polypeptide Conjugate Pharmaceutical Composition

This example shows a method of making a saccharide-polypeptide conjugate pharmaceutical composition. A capsular polysaccharide is isolated from a *H. influenzae* serotype c. The serotype a capsular polysaccharide is conjugated to a $CRM_{197}$ polypeptide. The saccharide-polypeptide conjugate is contacted with an excipient.

Example 14

Method of Making a Saccharide-Polypeptide Conjugate Pharmaceutical Composition

This example shows a method of making a saccharide-polypeptide conjugate pharmaceutical composition. A capsular polysaccharide is isolated from a *H. influenzae* serotype d. The serotype a capsular polysaccharide is conjugated to a $CRM_{197}$ polypeptide. The saccharide-polypeptide conjugate is contacted with an excipient.

Example 15

Method of Making a Saccharide-Polypeptide Conjugate Pharmaceutical Composition

This example shows a method of making a saccharide-polypeptide conjugate pharmaceutical composition. A capsular polysaccharide is isolated from a *H. influenzae* serotype e. The serotype a capsular polysaccharide is conjugated to a $CRM_{197}$ polypeptide. The saccharide-polypeptide conjugate is contacted with an excipient.

Example 16

Method of Making a Saccharide-Polypeptide Conjugate Pharmaceutical Composition

This example shows a method of making a saccharide-polypeptide conjugate pharmaceutical composition. A capsular polysaccharide is isolated from a *H. influenzae* serotype f. The serotype a capsular polysaccharide is conjugated to a $CRM_{197}$ polypeptide. The saccharide-polypeptide conjugate is contacted with an excipient.

This example shows the composition of a kit with a saccharide-polypeptide conjugate. A saccharide-polypeptide conjugate in a vial or a pre-filled syringe is placed in a container. The container is further associated with instructions of use.

Example 18

Method of Vaccination for Children Age Two Years or Under

This example shows vaccine compositions and a dosing schedule for the vaccine compositions for children age two years or under. An aqueous vaccine composition is composed of an immunogenic saccharide-lipid conjugate comprising capsular polysaccharides from the *H. influenzae* serotype a and α-galactosylceramide. The aqueous vaccine is formulated to contain from 1-5 microgram of each serotype and aluminum phosphate as an adjuvant.

A single 0.5 mL dose of the an aqueous vaccine is given by intramuscular injection to a child age two years or under at three or four different times. A single dose is given at age 2 months. A single dose is given at an age of at least 6 weeks.

Optionally, a single dose is given at 6 months. A single dose given at age 12 through 24 months.

Example 19

Method of Vaccination for Children Ages 2 Through 17 Years Old

This example shows vaccine compositions and a dosing schedule for the vaccine compositions for children ages 2 through 18 years old. An aqueous vaccine composition is composed of an immunogenic saccharide-lipid conjugate comprising capsular polysaccharides from the *H. influenzae* serotype a and α-galactosylceramide. The aqueous vaccine is formulated to contain from 1-5 microgram of each serotype and aluminum phosphate as an adjuvant.

A single 0.5 mL dose of the aqueous vaccine is given by intramuscular injection to a child who is age 2 through 18 years old.

Example 20

Composition and Method of Use of a Vaccination for Protection Against *H. influenzae* in the United States, Canada, Saudi Arabia, and Australia This example shows a vaccine composition that provides protection against *H. influenzae* for subjects in the United States, Canada, Saudi Arabia, and Australia. An aqueous vaccine composition is composed of an immunogenic saccharide-lipid conjugate comprising capsular polysaccharides from the *H. influenzae* serotype a and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease found in the United States, Canada, Saudi Arabia, and Australia is improved.

Example 21

Composition and Method of Use of a Vaccination for Protection Against *H. influenzae* in Europe and Australia This example shows a vaccine composition that provides protection against *H. influenzae* for subjects in the Europe and Australia. An aqueous vaccine composition is composed of an immunogenic saccharide-lipid conjugate comprising capsular polysaccharides from the *H. influenzae* serotype d, e, and f, and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease found in the Europe and Australia is improved.

Example 22

Composition and Method of Use of a Vaccination for Protection Against *H. influenzae* in Australia This example shows a vaccine composition that provides protection against *H. influenzae* for subjects in Australia. An aqueous vaccine composition is composed of an immunogenic saccharide-lipid conjugate containing capsular polysaccharides from the *H. influenzae* serotype a, d, e, and f, and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease found in Australia is improved.

Example 23

Composition and Method of Use of a Vaccination for Protection Against *H. influenzae* Serotype a This example shows a vaccine composition that provides protection against *H. influenzae*. An aqueous vaccine composition is composed of an immunogenic saccharide-lipid conjugate comprising capsular polysaccharides from the *H. influenzae* serotype a and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 24

Composition and Method of Use of a Vaccination for Protection Against *H. influenzae* Serotype b This example shows a vaccine composition that provides protection against *H. influenzae*. An aqueous vaccine composition is composed of an immunogenic saccharide-lipid conjugate comprising capsular polysaccharides from the *H. influenzae* serotype b and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 25

Composition and Method of Use of a Vaccination for Protection Against *H. influenzae* Serotype c This example shows a vaccine composition that provides protection against *H. influenzae*. An aqueous vaccine composition is composed of an immunogenic saccharide-lipid conjugate comprising capsular polysaccharides from the *H. influenzae* serotype a and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 26

Composition and Method of Use of a Vaccination for Protection Against *H. influenzae* Serotype d This example shows a vaccine composition that provides protection against *H. influenzae*. An aqueous vaccine composition is composed of an immunogenic saccharide-lipid conjugate comprising capsular polysaccharides from the *H. influenzae* serotype a and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 27

Composition and Method of Use of a Vaccination for Protection Against *H. influenzae* Serotype e This example shows a vaccine composition that provides protection against *H. influenzae*. An aqueous vaccine composition is composed of an immunogenic saccharide-lipid conjugate comprising capsular polysaccharides from the *H. influenzae* serotype a and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 28

Composition and Method of Use of a Vaccination for Protection Against *H. influenzae* Serotypes a, b, c, d, e, and f This example shows a vaccine composition that provides protection against *H. influenzae*. An aqueous vaccine composition is composed of an immunogenic saccharide-lipid conjugate comprising capsular polysaccharides from the *H. influenzae* serotype a, b, c, d, e, and f, and α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 29

Composition and Method of Use of a Vaccination for Protection Against *H. influenzae* Serotypes a and b This example shows a vaccine composition that provides protection against *H. influenzae*. An aqueous vaccine composition is composed of an immunogenic saccharide-lipid conjugate comprising capsular polysaccharides from the *H. influenzae* serotypes a and b, α-galactosylceramide. The aqueous vaccine is formulated to contain from 1-5 microgram of each serotype and aluminum phosphate as an adjuvant.

At least one single 0.5 mL dose of the aqueous vaccine is given by intramuscular injection to the subject. After administration, immunity of the subject against *H. influenzae* disease is improved.

Example 30

Method of Making a Saccharide-Lipid Conjugate Pharmaceutical Composition

This example shows a method of making a saccharide-lipid conjugate pharmaceutical composition. A capsular polysaccharide is isolated from a *H. influenzae* serotype a. The serotype a capsular polysaccharide is conjugated to α-galactosylceramide. The saccharide-lipid conjugate is contacted with an excipient.

Example 31

Method of Making a Saccharide-Lipid Conjugate Pharmaceutical Composition

This example shows a method of making a saccharide-lipid conjugate pharmaceutical composition. A capsular polysaccharide is isolated from a *H. influenzae* serotype b. The serotype a capsular polysaccharide is conjugated to α-galactosylceramide. The saccharide-lipid conjugate is contacted with an excipient.

Example 32

Method of Making a Saccharide-Lipid Conjugate Pharmaceutical Composition

This example shows a method of making a saccharide-lipid conjugate pharmaceutical composition. A capsular polysaccharide is isolated from a *H. influenzae* serotype c. The serotype a capsular polysaccharide is conjugated to α-galactosylceramide. The saccharide-lipid conjugate is contacted with an excipient.

Example 33

Method of Making a Saccharide-Lipid Conjugate Pharmaceutical Composition

This example shows a method of making a saccharide-lipid conjugate pharmaceutical composition. A capsular polysaccharide is isolated from a *H. influenzae* serotype d. The serotype a capsular polysaccharide is conjugated to α-galactosylceramide. The saccharide-polypeptide conjugate is contacted with an excipient.

Example 34

Method of Making a Saccharide-Lipid Conjugate Pharmaceutical Composition

This example shows a method of making a saccharide-lipid conjugate pharmaceutical composition. A capsular polysaccharide is isolated from a *H. influenzae* serotype e. The serotype a capsular polysaccharide is conjugated to α-galactosylceramide. The saccharide-lipid conjugate is contacted with an excipient.

Example 35

Method of Making a Saccharide-Lipid Conjugate Pharmaceutical Composition

This example shows a method of making a saccharide-lipid conjugate pharmaceutical composition. A capsular polysaccharide is isolated from a *H. influenzae* serotype f. The serotype a capsular polysaccharide is conjugated to α-galactosylceramide. The saccharide-lipid conjugate is contacted with an excipient.

Example 36

Composition of a Kit with a Saccharide-Lipid Conjugate

This example shows the composition of a kit with a saccharide-lipid conjugate. A saccharide-lipid conjugate in a vial or a pre-filled syringe is placed in a container. The container is further associated with instructions of use.

Example 37

Methods of Assessing Immunogenic Saccharide-Carrier Conjugates

Immunogenic saccharide-carrier conjugates comprising capsule polysaccharides from *H. influenzae* serotype a conjugated to a carrier, such as a polypeptide, are produced as described herein. For example, *H. influenzae* serotype a is grown in liquid medium and the supernatant of the culture may be precipitated to isolate the capsular polysaccharides. An example carrier polypeptide, $CRM_{197}$, may be obtained from commercial sources or obtained by culturing a *Corynebacterium diphtheria* strain expressing $CRM_{197}$. The *H. influenzae* serotype a saccharides and $CRM_{197}$, are activated and then conjugated as described, for example, in St. Michael et al. *Glycoconj. J.* (2014) 31:25-39, and may be assessed using mass spectrometry, NMR, and/or HPLC.

Rodents, such as rabbits may be immunized one or more times via subcutaneous injection, with the saccharide-carrier conjugates in combination with an adjuvant. The level of anti-saccharide antibodies is assessed by subjecting serum samples from the rodent to enzyme-linked immunosorbent assays. The functional activity of the antibodies may be assessed by subjecting serum samples from the rodents to bacteriocidal assays and/or opsonophagocytosis assays.

Cox et al. (*Vaccine* (2017) 35: 6129-6136), demonstrates that example saccharide-carrier conjugates comprising capsule polysaccharides from *H. influenzae* serotype a conjugated to $CRM_{197}$ carrier, as described herein, were successful in stimulating functional antibodies to *H. influenzae* serotype a.

While preferred embodiments have been shown and described herein, it will be apparent to those skilled in the art that such embodiments are provided by way of example only.

What is claimed is:

1. A pharmaceutical composition comprising
   (i) an immunogenic saccharide-glycosphingolipid conjugate comprising a *Haemophilus influenzae* serotype a capsular polysaccharide, fragment thereof, or combination thereof conjugated to a glycosphingolipid; or
   (ii) a plurality of at least two unique immunogenic saccharide-glycosphingolipid conjugates each comprising individually a capsular polysaccharide, fragment thereof, or combination thereof conjugated to a glycosphingolipid,
   wherein at least one of the capsular polysaccharides, fragment thereof, or combination thereof is from *Haemophilus influenzae* serotype a, and
   wherein at least one of the capsular polysaccharides, fragment thereof, or combination thereof is from a *Haemophilus influenzae* serotype selected from the group consisting of serotypes b, c, d, e, and f.

2. The pharmaceutical composition of claim 1, wherein the fragment of the capsular polysaccharide comprises a monosaccharide, a disaccharide, a trisaccharide, a tetrasaccharide, a pentasaccharide, a hexasaccharide, or an oligosaccharide.

3. The pharmaceutical composition of claim 1, wherein the glycosphingolipid is a cerebroside comprising a ceramide with a galactose residue at the 1-hydroxyl group moiety; and/or wherein the glycosphingolipid is α-galactosylceramide.

4. The pharmaceutical composition of claim 1, wherein the capsular polysaccharide or fragment thereof, or combination thereof is conjugated to the glycosphingolipid via a covalent bond.

5. The pharmaceutical composition of claim 1, wherein the capsular polysaccharide or fragment thereof, or combination thereof is conjugated via a linker to the glycosphingolipid.

6. The pharmaceutical composition of claim 1, wherein the glycosphingolipid is conjugated to one serotype of capsular polysaccharide, fragment thereof, or combination thereof.

7. The pharmaceutical composition of claim 1, wherein the glycosphingolipid is conjugated to two or more serotypes of the capsular polysaccharide, fragment thereof, or combination thereof.

8. The pharmaceutical composition of claim 1, further comprising an adjuvant; a chelating agent; a surfactant, an emulsifier; a buffering agent; a preservative; a salt; an anti-fungal compound or a salt of an anti-fungal compound; or a combination thereof.

9. The pharmaceutical composition of claim 1, wherein the pharmaceutical composition is in the form of an intramuscularly injectable composition, intradermally injectable composition, subcutaneously injectable composition, or an intranasally administrable composition.

10. The pharmaceutical composition of claim 1, wherein the immunogenic saccharide-glycosphingolipid conjugate induces functional *H. influenzae* serotype a-specific IgG antibodies.

11. The pharmaceutical composition of claim 1, wherein when the pharmaceutical composition is administered to a human, the pharmaceutical composition elicits an immune response.

12. The pharmaceutical composition of claim 1, wherein the plurality of unique immunogenic saccharide-glycosphingolipid conjugates comprises capsular polysaccharides from *H. influenzae* serotypes a and b, or wherein the plurality of unique immunogenic saccharide-glycosphingolipid conjugates comprises capsular polysaccharides from *H. influenzae* serotypes a and f.

13. The pharmaceutical composition of claim 1, wherein the immunogenic saccharide-glycosphingolipid conjugate is individually present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the composition.

14. A method of eliciting an immunoprotective antibody response, comprising administering the saccharide-glycosphingolipid conjugate of claim 1, or any fragment thereof to a subject.

15. A method comprising administering to a subject a first composition, wherein the first composition is the pharmaceutical composition of claim 1.

16. A method of making a composition comprising contacting the immunogenic saccharide-glycosphingolipid conjugate of claim 1 with an excipient, an adjuvant, or any combination thereof.

17. The method of claim 16, wherein the composition is injectable or intranasally administrable.

18. The method of claim 16, wherein the composition is in a form of a vaccine.

19. The method of claim 16, wherein the immunogenic saccharide-glycosphingolipid conjugate is individually present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the composition.

20. A kit comprising of a pharmaceutical composition of claim 1 contained in a container.

* * * * *